US006583115B1

(12) United States Patent
Kopchick et al.

(10) Patent No.: US 6,583,115 B1
(45) Date of Patent: *Jun. 24, 2003

(54) METHODS FOR TREATING ACROMEGALY AND GIANTISM WITH GROWTH HORMONE ANTAGONISTS

(75) Inventors: John J. Kopchick, Athens, OH (US); Wen Y. Chen, Athens, OH (US)

(73) Assignee: Ohio University/Edison Biotechnology Institute, Athens, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/486,793

(22) Filed: Jun. 7, 1995

Related U.S. Application Data

(63) Continuation-in-part of application No. 08/313,505, filed on Sep. 26, 1994, which is a continuation of application No. 07/878,703, filed on May 4, 1992, now Pat. No. 5,350,836, which is a continuation-in-part of application No. 07/693,305, filed on May 1, 1991, now abandoned, which is a continuation-in-part of application No. PCT/US90/05874, filed on Oct. 12, 1990, now abandoned, which is a continuation-in-part of application No. 07/419,561, filed on Oct. 12, 1989, now abandoned.

(51) Int. Cl.[7] .......................... A61K 38/27; C07K 14/61
(52) U.S. Cl. ............................... 514/12; 514/2; 530/399
(58) Field of Search ..................... 530/350, 399; 930/120; 514/2, 12; 435/69.4

(56) References Cited

U.S. PATENT DOCUMENTS

| | | | |
|---|---|---|---|
| 3,664,925 A | 5/1972 | Sonenberg et al. | |
| 4,056,520 A | 11/1977 | Sonenberg et al. | |
| 4,443,539 A | 4/1984 | Fraser et al. | |
| 4,871,835 A | 10/1989 | Aviv et al. | ............ 530/399 |
| 5,079,345 A | 1/1992 | Becker et al. | |
| 5,580,723 A | * 12/1996 | Wells et al. | ............ 435/6 |

FOREIGN PATENT DOCUMENTS

| | | |
|---|---|---|
| EP | 75444 | 9/1982 |
| EP | 103395 | 8/1983 |
| EP | 161640 | 5/1985 |
| EP | 193515 | 2/1986 |
| GB | 2073245 | 3/1981 |
| WO | US90/05874 | 10/1990 |
| WO | US90/03550 | 1/1991 |
| WO | 9100870 | 1/1991 |
| WO | US92/03743 | 5/1992 |
| WO | 9219736 | 11/1992 |

OTHER PUBLICATIONS

The Merck Manual, Ed. Berkow, R. Merck & Co, Inc. N.J., pp. 993–994, 1982.*
Mode et al. Endocrinol. 137(2):447–454, 1996.*
George et al. Macromolec. Seq. & Syn. pp. 127–149, 1988.*
Brems et al., 1987, "Helical formation in isolated fragments of bovine growth hormone", Biochemistry 26:7774–7778.

Swislocki et al., 1970, "In vitro metabolic effects of bovine growth hormone fragments in adipose tissue", Endocrinology 87:900–904.
Paladini et al., 1979, "The intriguing nature of the multiple actions of growth hormone", TIBS 256–260.
Hara et al., 1978, "Recombination of the biologically active peptides from a tryptic digest of bovine growth hormone", Biochemistry 17:550–556.
Chen and Sonenberg, 1977, "Revision of the amino acid sequence of an active fragment of bovine growth hormone", J. Biol. Chem. 250:2510–2514.
Hammer et al., 1985, "Production of transgenic rabbits, sheep and pigs by microinjection", Nature 315:680–683.
Palmiter et al., 1982, "Dramatic growth of mice that develop from eggs microinjected with metallothionein—growth hormone fusion genes", Nature 300:611–615.
Palmiter et al., 1983, "Metallothionein–Human GH fusion genes stimulate growth of mice", Science 222:809–814.
Hammer, 1985, "Expression of human growth hormone–releasing factor in transgenic mice results in increased somatic growth", Nature 315:413–416.
McGrane et al., 1988, "Tissue–specific expression and dietary regulation of a chimeric phosphoenolpyruvate carboxykinase/bovine growth hormone gene in transgenic mice", J. Biol. Chem. 263:11443–11451.
Kopchick et al., 1989, "Direct DNA transfer and molecular approaches to animal growth", Brazil. J. Genetics 12:37–54.
Chou and Fasman, 1974, "Prediction of protein conformation", Biochemistry 13:222–245.
Kaiser, 1987, "Design of amphiphilic peptides", in: Protein Engineering (Oxender and Fox, eds) 193–199.
DeGrado et al., 1981, "Design, synthesis and characterization of a cytotoxic peptide with melittin–like activity", J. Am. Chem. Soc. 103:679–681.
DeGrado et al., 1982, "Kinetics and mechanism of hemolysis induced by melittin and by a synthetic melittin analogue", Biophys. J. 37:339–338.

(List continued on next page.)

Primary Examiner—Christine J. Saoud
(74) Attorney, Agent, or Firm—Iver P. Cooper

(57) ABSTRACT

The present invention relates to antagonists of vertebrate growth hormones obtained by mutation of the third alpha helix of such proteins (especially bovine or human GHs). These mutants-have growth-inhibitory or other GH-antagonizing effects. These novel hormones may be administered exogenously to animals, or transgenic animals may be made that express the antagonist. Animals have been made which exhibited a reduced growth phenotype. The invention also describes methods of treating acromegaly, gigantism, cancer, diabetes, vascular eye diseases (diabetic retinopathy, retinopathy of prematurity, age-related macular degeneration, retinopathy of sickle-cell anemia, etc.) as well as nephropathy and other diseases, by administering an effective amount of a growth hormone antagonist. The invention also provides pharmaceutical formulations comprising one or more growth hormone antagonists.

9 Claims, 12 Drawing Sheets

OTHER PUBLICATIONS

Tou et al., 1986, "Amphiphilic growth hormone releasing factor (GRF) analogs: Peptide design and biological activity in vivo", Biochem. Biophys. Res. Comm. 139:763–770.

Brems et al., 1988, "Stabilization of an associated folding intermediate of bovine growth hormone by site–directed mutagenesis", Proc. Natl. Acad. Sci 85:3367–3371.

Smith and Talamantes, 1987, "Identification and characterization of heterogenous population of growth hormone receptors", J. Biol. Chem. 262:2213–2219.

Sporn et al., 1986, "Transforming growth factor–beta: Biological function and chemical structure", Science 233:532–534.

Chen et al., 1990, "Expression of a mutated bovine growth hormone gene suppresses growth of transgenic mice", Proc. Natl. Acad. Sci. 87:5061–5065.

Alan R. Liss Inc., 1987, "Protein Engineering", pp. 193–199.

Cunningham et al., 1989, "Receptor and antibody epitopes in human growth hormone identified by homolog–scanning mutagenesis", Science 243:1330–1336.

Chen et al., 1992, "Conversion of bovine growth hormone cysteine residues to serine affects secretion by cultured cells and growth rates in transgenic mice", Mol. Endocrinology 6:598–606.

Chen et al., 1991, "Functional antagonism between endogenous mouse growth hormone (GH) and a GH analog results in dwarf transgenic mice", Endocrinology 129:1402–1408.

Chen et al., 1991, "Glycine 119 of bovine growth hormone is critical for growth promoting activity" Mol. Endocrinology 5:1845–1852.

Chen et al., 1991, "Mutations in the third α–helix of bovine growth hormone dramatically affect its intracellular distribution in vitro and growth enhancement in transgenic mice", J. Biol. Chem. 266:2252–2258.

Chen et al., 1992, "Receptor binding mitogenic activity and transgenic mouse studies on bGH–hGH analogs", FASEB J. 6:A1344.

Chen et al., 1992, "Substitution mutations of Lysine–64 (K64) of bovine growth hormone (bGH) affect receptor binding affinities and growth rates of transgenic mice", FASEB J. 5:A424.

Cunningham et al., High resolution epitope mapping of hGH–receptor interactions by alanine scanning mutagenesis, Science 244:1081–1085.

Goeddel et al., 1979, "Direct expression in *Escherichia Coli* of a DNA sequence coding for human growth hormone", Nature 281:544–548.

Kopchick and Cioffi, 1991, "Exogenous and endogenous effects of growth hormone in animals", Livest. Prod. Sci. 27:61–75.

McAndrew et al., 1991, "Effects of a leucine analog on growth hormone processing and secretion by cultured cells", J. Biol. Chem. 266:15016–15020.

McAndrew et al., 1991, "Expression of truncated forms of the bovine growth hormone gene in cultured mouse cells", J. Biol. Chem. 266:20956–20969.

Okada et al., 1992, "A growth hormone (GH) analog can antagonize the ability of native GH to promote differentiation of 3T3–F442A preadipocytes and stimulate insulin–like and lipolytic activities in primary rat adipocytes", Endocrinology 130:2284–2290.

Okada et al., Antagonism of bovine growth hormone (bGH) stimulated glucose–transport by a bGH analog in 3T3–F442A adipose cells, FASEB J. 6:PA 1272.

Parks et al., 1992, "Structural–functions studies of the first alpha–helix of bovine growth hormone", FASEB J. 6:A1345.

Seeberg et al., 1992, "Efficient bacterial expression of bovine and porcine growth hormone", DNA 2(1):37–45.

Watahiki et al., 1989, "Conserved and unique amino acid residues in the domains of the growth hormone", J. Biol. Chem.

Fuh et al., 1992, "Rational design of potent antagonists to the human growth receptor", Science 256:1677–1680.

Yamasaki et al., 1975, "Studies on the common active site of growth hormone. Revision of the amino acid sequence of an active fragment of bovine growth hormone", J. Biol. Chem. 250(7):2510–2514.

Zoller and Smith, 1987, "Oligonucleotide directed mutagenesis: A simple method using two oligonucleotide primers and a single–stranded DNA template", Methods Enzymol. 154:329–350.

Bell et al., 1991, "Diabetic nephropathy: Changing concepts of pathogenesis and treatment", Am J Med Sci 301(3):195–200.

Bratusch–Marrain et al., 1982, "The effect of growth hormone on glucose metabolism and insulin secretion in man", J Clin Endocrinol Metab 55(5):973–982.

Chang et al., 1987, "High–level secretion of human growth hormone by *Escherichia coli*", Gene 55:189–196.

Chen et al., 1994, "In vitro and vivo studies of antagonistic effects of human growth hormone analogs", J Biol Chem 269(22):15892–15897.

Chen et al., 1995, "Effects of streptozoticin treatment in growth hormone (GH) and GH antagonist transgenic mice", Endocrinology 136(2):660–667.

DeNoto et al., 1981, "Human growth hormone DNA sequence and mRNA structure: Possible alternative splicing", Nucleic Acids Res 9(15):3719–3730.

Doi et al., 1990, "Glomerular lesions in mice transgenic for growth hormone and insulinlike growth factor–1", Am J Pathol 137(3):541–552.

Doi et al., 1988, "Progressive glomerulosclerosis develops in transgenic mice chronically expressing growth hormone and growth hormone releasing factor but not in those expressing insulinlike growth factor–1", Am J Pathol 131(3):398–403.

Foley et al., 1995, "The effect of growth hormone on a mouse model of proliferative retinopathy", Invest Ophthamol Visual Sci 36(4):Abstract.

Froesch et al., 1985, "Actions of insulin–like growth factors", Ann Rev Physiol 47:443–467.

Gerich, 1984, "Role of growth hormone in diabetes mellitus", New Engl J Med 310(13):848–850.

Graf et al., 1976, "Action of thrombin on ovine, bovine and human pituitary growth hormones", Eur J Biochem 64:333–340.

Leung et al., 1986, "Purification and physiochemical properties of a recombinant bovine growth hormone produced by cultured murine fibroblasts", Endocrinol 119(4):1489–1496.

MacGorman et al., 1981, "Physiological concentrations of growth hormone exert insulin–like and insulin antagonistic effects on both hepatic and extrahepatic tissues in man", J Clin Endocrinol Metab 53(3):556–559.

Melmed et al., 1994, "Consensus Statement: Benefits versus risks of medical therapy for acromegaly", Am J Med 97:468–473.

Mercado et al, 1994, "Distribution of growth hormone receptor messenger ribonucleic acid containing and lacking exon 3 in human tissues", J Clin Endocrinol Metab 78(3):731–735.

Merimee, 1978, "A follow–up study of vascular disease in growth–hormone–deficient dwarfs with diabetes", New Engl J Med 298(22):1217–1222.

Miller et al., 1980, "Molecular cloning of DNA complementary to bovine growth hormone mRNA", J Biol Chem 255(16):7521–7524.

Ng et al., 1974, "Insulin potentiating action of synthetic peptides relating to the amino terminal sequence of human growth hormone", Diabetes 23(12):943–949.

Pesce et al., 1991, "Glomerulosclerosis at both early and late stages is associated with increased cell turnover in mice transgenic for growth hormone", Lab Invest 65(5):601–605.

Press et al., 1984, "Importance of raised growth hormone levels in mediating the metabolic derangements of diabetes", New Engl J Med 310(13):810–814.

Robins et al., 1982, "Regulated expression of human growth hormone genes in mouse cells", Cell 29:623–631.

Rymaszewski et al., 1991, "Human growth hormone stimulates proliferation of human retinal microvascular endothelial cells in vitro", Proc Natl Acad Sci USA 88:617–621.

Stewart et al., 1992, "An evaluation of the functions of the 22–kilodalton (kDa), and the 20–kDa, and the N–terminal polypeptide forms of human growth hormone using transgenic mice", Endocrinol 130(1):405–414.

Strobl and Thomas, 1994, "Human growth hormone", Pharmacological Reviews 46(1):1–34.

Vance and Harris, 1991, "Long–term treatment of 189 acromegalic patients with the somatostatin analog octreotide", Arch Intern Med 151:1573–1578.

Weigent and Blalock, 1995, "Growth hormone effects on the immune system", in *Human Growth Hormone Pharmacology: Basic and Clinical Aspects,* Shiverick and Rosenbloom (eds.) pp. 141–151.

Woychick et al., 1982, "Cloning and nucleotide sequencing of the bovine growth hormone gene", Nucleic Acids Res 10(22):7197–7210.

Yang et al., 1993, "Glomerulosclerosis in mice transgenic for native or mutated bovine growth hormone gene", Kidney International vol. 43, Suppl. 39, pp. S90–S94.

Yang et al., 1993, "Glomerulosclerosis and body growth are mediated by different portions of bovine growth hormone", Lab Invest 68(1):62–70.

Zapf and Froesch, 1986, "Insulin–like growth factors/somatomedins: Structure, secretion, biological actions and physiological role", Hormone Res 24:121–130.

Guyton, Textbook of Medical Physiology, Eighth Edition, Philadelphia: W.B. Saunders Company, pp. 826–827.

Rymaszewski, et al., Human Growth Hormone Stimulates Proliferation of Human Retinal Microvascular Endothelial Cells in vitro, Proc. Natl. Acad. Sci. USA, vol. 88, pp. 617–621, Jan. 1991.

Stephens, Robert F. M.D., Proliferative Sickle Cell Retinopathy: The Disease and a Review of its Management, Surgical Reviews, vol. 18, No. 3, pp. 222–231, Mar. 1987.

* cited by examiner

```
ATGATGGCTGCAGGCCCCCGGACCTCCCTGCTCCTGGCTTTCGCCCTGCTCTGCCTGCCC
 M  M  A  A  G  P  R  T  S  L  L  L  A  F  A  L  L  C  L  P
         -20                                        10
                  I─────────────────────────────────────────
TGGACTCAGGTGGTGGGCGCCTTCCCAGCCATGTCCTTGTCCGGCCTGTTTGCCAACGCT
 W  T  Q  V  V  G  A  F  P  A  M  S  L  S  G  L  F  A  N  A
─────────── Helix I ──────────────────────────────────────── I
GTGCTCCGGGCTCAGCACCTGCATCAGCTGGCTGCTGACACCTTCAAAGAGTTTGAGCGC
 V  L  R  A  Q  H  L  H  Q  L  A  A  D  T  F  K  E  F  E  R
         20                                         30
ACCTACATCCCGGAGGGACAGAGATACTCCATCCAGAACACCCAGGTTGCCTTCTGCTTC
 T  Y  I  P  E  G  Q  R  Y  S  I  Q  N  T  Q  V  A  F  C  F
         40                                         50
                              I ─────────── Helix II ───
TCTGAAACCATCCCGGCCCCCACGGGCAAGAATGAGGCCCAGCAGAAATCAGACTTGGAG
 S  E  T  I  P  A  P  T  G  K  N  E  A  Q  Q  K  S  D  L  E
         60                                         70
──────────────── I
CTGCTTCGCATCTCACTGCTCCTCATCCAGTCGTGGCTTGGGCCCCTGCAGTTCCTCAGC
 L  L  R  I  S  L  L  L  I  Q  S  W  L  G  P  L  Q  F  L  S
         80                                         90
                              I ─────────────
AGAGTCTTCACCAACAGCTTGGTGTTTGGCACCTCGGACCGTGTCTATGAGAAGCTGAAG
 R  V  F  T  N  S  L  V  F  G  T  S  D  R  V  Y  E  K  L  K
         100                                        110
─────── Helix III ─────────── I
GACCTGGAGGAAAGGATCCTGCCCCTGATGCGGGAGCTGGAAGATGGCACCCCCCGGGCT
 D  L  E  E  R  I  L  A  L  M  R  E  L  E  D  G  T  P  R  A
         120                                        130
                                          I ────────────
GGGCAGATCCTCAAGCAGACCTATGACAAATTTGACACAAACATGCGCAGTGACGACGCG
 G  Q  I  L  K  Q  T  Y  D  K  F  D  T  N  M  R  S  D  D  A
         140                                        150
                  ──────────── Helix IV ──────────────────
CTGCTCAAGAACTACGGTCTGCTCTCCTGCTTCCGGAAGGACCTGCATAAGACGGAGACG
 L  L  K  N  Y  G  L  L  S  C  F  R  K  D  L  H  K  T  E  T
         160                                        170
──────────── I
TACCTGAGGGTCATGAAGTGCCGCCGCTTCGGGGAGGCCAGCTGTGCCTTCTAG
 Y  L  R  V  M  K  C  R  R  F  G  E  A  S  C  A  F  END
         180                                        190
```

FIG.1

METHODS FOR TREATING ACROMEGALY AND GIANTISM WITH GROWTH HORMONE ANTAGONISTS

CROSS-REFERENCE TO RELATED APPLICATIONS

This application is a continuation-in-part of application Ser. No. 08/313,505, filed Sep. 26, 1994, which is a continuation of application Ser. No. 07/878,703, filed May 4, 1992, now U.S. Pat. No. 5,350,836, which is a continuation-in-part of application Ser. No. 07/693,305, filed May 1, 1991, abandoned, which is a continuation-in-part of PCT application Ser. No. PCT/US90/05874, filed Oct. 12, 1990, abandoned, which is a continuation-in-part of application Ser. No. 07/419,561, filed Oct. 12, 1989, abandoned, all of which are hereby incorporated by reference herein.

FIELD OF THE INVENTION

This invention relates to novel muteins of growth hormone ("GH"), especially human growth hormone ("hGH"), which diminish, decrease or inhibit the growth of animals or otherwise diminish, decrease or inhibit the effects of endogenous GH by acting as an antagonist to growth hormone receptors ("GHRs"). This invention also relates to DNAs encoding such muteins as well as methods for the treatment of diseases and disorders that are wholly or partially mediated by GHRs using a GH antagonist.

BACKGROUND OF THE INVENTION hGH and bovine growth hormone ("bGH") are proteins of about 191 amino acids that are naturally synthesized in the anterior lobe of the pituitary. The molecular weight of the mature proteins is about 22,000 daltons, but they are initially made as pre-GHs with an extra 26 amino acids at the amino-terminus. This leader (or signal peptide) is-normally cleaved during secretion by pituitary cells to release the mature form.

Several forms of mature bGH have been found in nature. The amino-terminus can vary (due to variation in the site of cleavage during secretion) so that the mature protein begins with either $NH_2$-Ala-Phe-Pro or $NH_2$-Phe-Pro, the latter referred to as "(des Ala) bGH". Additionally, the amino acid at bGH position 126 may be either Leu or Val, apparently as a result of allelic variation in the bovine population.

Exogenous administration of bGH to cattle increases milk production, feed efficiency, growth rate, and the lean-to-fat ratio, and decreases fattening time.

bGH has been produced by recombinant DNA techniques, see, e.g., Fraser, U.S. Pat. No. 4,443,539 (yeast); Buell, EP Appl. No. 103,395 (bacteria); Krivl, EP Appl. No. 193,515 (bacteria); Kopchick, EP Appl. No. 161,640 (encapsulated mouse cells implanted into animals); DeBoer, EP Appl. No. 75,444 (bacteria; gene modified to eliminate harmful secondary structure) and this has facilitated the production of analogues of bGH by site-specific mutagenesis. Thus, Aviv, GB No. 2,073,245 describes production of Met-Pro (des Ala) bGH, Met-Arg (des Ala) bGH, Met-Glu-Gly (des Ala) bGH, and des (Ala1-Phe2-Pro3-Ala4) bGH in *E. coli*. Brems et al., Proc. Natl. Acad. Sci. USA 85:3367–71 (1988) reported preparation of the bGH mutant K112L, which extended the hydrophobic face of the third alpha helix of bGH. The bGH (96–133) fragment of this mutant was also prepared.

The biological activity of proteolytic fragments of bGH has also been studied. Brems et al., Biochemistry 26:7774 (1987); Swislocki et al., Endocrinology 87:900 (1970); Paladini et al., TIBS 256 (Nov. 1979). The fragment bGH (96–133) is superior in growth-promoting assays to bGH (1–95) and bGH (151–191). Hara et al., Biochemistry 17:550 (1978); Sonenberg, U.S. Pat. Nos. 3,664,925 and 4,056,520; Chen and Sonenberg, J. Biol. Chem. 250:2510–14 (1977). An octapeptide derived from the amino-terminus of bGH has been shown to have hypoglycemic activity, see Ng et al., Diabetes 23:943–949 (1974), but it has no effect on growth. Similar results were observed with the fragment bGH (96–133). Graf et al., Eur. J. Biochem. 64:333–340 (1976); Hara et al., Biochem. 17:550–56 (1978).

Analogues of bGH have varied in growth-promoting activity, as have the known analogues of other GHs. However, a GH analogue having growth-inhibitory activity has not been previously been reported.

A variety of transgenic animals have been produced. Hammer et al., Nature 315:680–638 (1985) (rabbits, sheep and pigs). Certain of these animals have been caused to express a GH, and increased growth of such transgenic animals has been reported. Palmiter et al., Nature 300:611 (1982) microinjected the male pronucleus of fertilized mouse eggs with a DNA fragment containing the promoter of the mouse metallothionein I gene fused to the structural gene of rat GH. Several of the transgenic mice developed from the genetically modified zygote exhibited a growth rate substantially higher than that of control mice. (In effect, the genetically modified mouse serves as a test environment for determining the effect of the hormone on animal growth). Later, Palmiter et al., Science 222:809 (1983) demonstrated that a similar enhancement of growth could be obtained in transgenic mice bearing an expressible hGH gene. A like effect is observed when hGH releasing factor is expressed in transgenic mice. Hammer, et a., Nature 315:413 (1985).

hGH and bGH have also been expressed in transgenic animals. McGrane et al., J. Biol. Chem. 263:11443–51 (1988); Kopchick et al., Brazil. J. Genetics 12:37–54 (1989); Chen et al., J. Biol. Chem. 269:15892–97 (1994). However, transgenic animals characterized by an exogenous gene which confers a reduced growth phenotype were hitherto unknown.

Abnormally high GH levels have been associated with a number of disorders. The two classic disorders which are directly caused by high levels of GH are acromegaly and gigantism.

Changes associated with acromegaly include coarsening of body hair, thickening and darkening of the skin, enlargement and overactivity of sebaceous and sweat glands such that patients frequently complain of excessive perspiration and offensive body odor, overgrowth of the mandible, cartilaginous proliferation of the larynx causing a deepening of the voice, and enlargement of the tongue. In addition, excess GH in these patients is responsible for proliferation of articular cartilage which may undergo necrosis and erosion and endoneural fibrous proliferation which causes peripheral neuropathies. Excess GH also increases tubular reabsorption of phosphate and leads to mild hyperphosphatemia. Many of these symptoms are also seen in patients with gigantism.

The hallmark of treatments for acromegaly and giantism is their ability to lower insulin-like growth factor-1 ("IGF-1") in plasma and/or tissue through either destruction of the pituitary or drug treatment. The role of IGF-1 in GH-mediated disorders, such as acromegaly and giantism is well recognized. Melmed et al., Amer. J. Med. 97:468–473 (1994).

The mainstay treatment modalities for these two disorders are pituitary ablation, radiation treatment, and bromocriptine mesylate. Pituitary ablation is a surgical procedure and, like any surgical procedure, is associated with a significant risk of complications including mortality. There are also risks associated with radiation treatment of the pituitary as well. In addition, the efficacy of radiation treatment may be delayed for several years. Moreover, these treatment modalities are not specific against that part of the pituitary that produces GH and may adversely affect adjacent tissue as well. Bromocriptine mesylate is a dopamine like drug which suppresses the production of GH. Recently, octreotide, a long-acting somatostatin analog has also been used to treat patients with acromegaly and gigantism which is refractory to surgery, radiation, and/or bromocriptine mesylate. Somatostatin inhibits the release of GH releasing hormone from the hypothalamus. GH releasing hormone stimulates production of GH in the pituitary and its secretion.

Another disorder that has been associated with abnormal GH levels is diabetes mellitus (DM). Characteristically, patients with poorly controlled DM have been found to have high levels of circulating GH. It has been shown that hypophysectomy could reduce diabetic hyperglycemia, thus strongly implicating the role of GH as an active component of the metabolic derangements of diabetes. Houssay and Biasotti, Rev. Soc. Argent. Biol. 6:251–296 (1930). It has been suggested that hypersecretion of GH may be the cause as much as the consequence of poor diabetic control. Press et al., New England J. Med. 310:810–814 (1984).

Most diabetics do not die of acute hyperglycemia. The overwhelming majority of diabetics die from complications associated with diabetes such as end organ failure. While diabetes affects almost all organs, heart and kidney failure are the most common causes of death. Other organs or systems that are commonly affected by DM are the eyes, the blood vessels and the nervous system. Patients with long standing diabetes will commonly have diabetic retinopathy, angiopathy and peripheral neuropathy. It is possible that normal GH secretion has a permissive role in patients predisposed to severe diabetic retinopathy. In such patients and in others in whom attempts to optimize glycemic control are unsuccessful, pharmacologic intervention may be beneficial not only in improving glycemic control but also in preventing severe proliferative diabetic retinopathy. Gerich et al., New England J. Med. 310:848–850 (1984).

Proliferative diabetic retinopathy is one of the leading causes of blindness in the United States and ranks second only to senile macular degeneration as a cause of permanent blindness. Benson et al., *Diabetic Retinopathy*, Duane, T., (eds.), Harper & Row, Philadelphia, Pa. pp. 1–24. In juveniles with insulin dependent diabetes, there is no evidence of diabetic retinopathy up to 5 years. However, 27% of juveniles who have had diabetes for 5 to 10 years have diabetic retinopathy. Also 71% of juveniles who have had diabetes for longer than 10 years have diabetic retinopathy. Greater than 90% of juveniles who have diabetes for 30 years will ultimately have diabetic retinopathy. Also, the 5 year mortality rate for individuals blind from diabetic retinopathy is 36%, in which death generally is caused by cardiac or kidney complications.

The pathogenesis of proliferative diabetic retinopathy is believed to be mediated by GH. It has been shown that human GH stimulates proliferation of human retinal microvascular endothelial cells in the diabetic; proliferation of these cells is the primary cause of proliferative diabetic retinopathy. Rymaszewski et al., Proc. Natl. Acad. Sci. USA 88:617–621 (1991). Thus, the involvement of GH in end organ damage in the diabetic is well established. Smith et al., Abstract of Presentation at ARVO meeting (May, 1995).

The kidneys are another organ that is affected by DM. Chen et al., Endocrinology 136:660–667 (1995). One type of pathology seen in patients with diabetic nephropathy is glomerulosclerosis. Glomerulosclerosis is the sclerosis of mesangial cells which is preceded by mesangial cell proliferation. Glomerular cells are responsible for filtering the blood and thus directly affect kidney function.

Transgenic mice which express bGH have been shown to have enlarged glomeruli which progressed to a state of glomerulosclerosis. Thus, GH has been implicated in the development of diabetic glomerulosclerosis. Doi et al., Am. J. Pathol. 137:541 (1990); Bell, Am. J. Med. Sci. 301:195 (1991).

The hypothesis that high levels of GH are responsible for many of the proliferative types of diseases seen in diabetics is further supported by the fact that dwarfs with diabetes do not develop the proliferative types of diseases seen in normal-sized diabetics. Merimee et al., New England J. Med. 298:1217–1222 (1978).

SUMMARY OF THE INVENTION

The present invention relates to proteins which are substantially homologous with a vertebrate GH but have growth-inhibitory activity.

We have discovered that mutation of Gly-119 in bGH to Arg ("G119R"), Pro ("G119P"), Lys ("G119K"), Trp ("G119W") or Leu ("G119L"), or the homologous Gly-120 in hGH to Arg ("G120R") or Trp ("G120W"), results in a mutein (mutant protein or peptide fragment thereof) which has growth-inhibitory activity in vertebrates, especially mammals. These novel hormones may be administered to mammals (or other vertebrates), in particular humans and bovines, when growth inhibition is desirable.

In one embodiment of the invention, the hormone is produced exogenously and administered to the subject. In view of the size of the hormone, it is preferably produced by expression in a suitable host of a genecoding for it. Such a gene is most readily prepared by site-specific mutagenesis of a bGH gene. However, the hormone may also be produced by other techniques, such as by condensation of fragments of native bGH with a synthetic peptide carrying the replacement of amino acid. If a peptide fragment has the desired growth-inhibitory activity, it may be prepared in toto by a Merrifield-type synthesis.

In a second embodiment of the invention, this gene is introduced into a prenatal form of a mammal by known techniques, and the prenatal form is developed into a transgenic mammal which expresses a reduced growth phenotype. Conceivably, a mammal could be genetically modified after birth, i.e., "gene therapy" and/or "gene/cell therapy".

Thus, growth-inhibited animals may be produced either by administration of the growth-inhibitory hormone of this invention in pharmaceutical form, or by genetic transformation of a prenatal or postnatal form of the animal.

The growth-inhibitory hormone, or the gene encoding it, is useful in the production of small animals for use in research facilities where space is restricted, as pets for pet lovers with limited quarters, and as livestock for farmers having small tracts.

The hormone may also be useful in the treatment of human gigantism, and in research on gigantism and dwarfism, in the treatment of diabetes and its sequelae, in the control of cholesterol, and in the prevention and treatment of certain cancers, particularly those whose growth is facilitated by GH or insulin-like growth factor-1 ("IGF-1").

In general, GH antagonists are therapeutically or prophylactically useful in countering the adverse effects of elevated levels of GHs, both endogenous hormones and hormones administered clinically.

In the course of our work, we have discovered a correlation between the ability of mouse L cells to secrete the protein and the protein having an effect (positive or negative) on growth rate in a transgenic animal. The use of an L cell secretion assay to identify growth-modulating proteins is also a part of this invention.

Another aspect of the invention is to provide methods for the treatment of various diseases involving the production of excess GH, wherein the methods comprise the step of administering an effective amount of a GH antagonist. Specifically, the invention provides methods of treating acromegaly, gigantism, cancer, diabetes, vascular eye diseases (diabetic retinopathy, retinopathy of prematurity, age-related macular degeneration, retinopathy of sickle-cell anemia, etc.) as well as nephropathy.

Another aspect of the invention is to provide pharmaceutical formulations for the treatment of diseases, wherein the formulation comprise at least one GH antagonist. The formulations may be adapted for the treatment of specific diseases and adapted for the administration to specific body sites.

More specifically, the present invention relates to a method for treatment of disorders or diseases which are wholly or partially regulated by GHRs using an antagonist to GHRs. One example of the antagonist used in the present invention are proteins which are substantially homologous with a vertebrate GH but have growth-inhibitory activity. However, any antagonist of GHRs can be used in the method of the present invention.

The disorders or diseases which can be treated by the method of the present invention are many. Any disorder or disease that is exacerbated by the action of an agonist on GHRs can be treated by the present invention.

In one embodiment of the present invention, the disorder is acromegaly or gigantism. Specifically, the invention includes methods for treating acromegaly and/or giantism by administering to patients having such disorders a therapeutically effective amount of a growth hormone antagonist together with a pharmaceutically acceptable carrier to reduce a pathological effect or symptom of acromegaly and.or giantism and, in particular, to lower levels of IGF-1 in plasma and/or tissue. The pathological effects and symptoms of these disorders are discussed above.

In another embodiment, the disease is diabetes mellitus (DM). More specifically, the method of the present invention is used to prevent or reduce proliferative diseases associated with diabetes such as diabetic retinopathy and glomerulosclerosis in patients with DM. In particular, such methods include administering a growth hormone-antagonist in a therapeutically effective amount to reduce a pathological effect or symptom of diabetes, such as nephropathy or retinopathy, and/or to lower blood glucose levels.

Additionally,. GH is well known to possess anti-insulin or diabetogenic activities which involves the ability of GH to inhibit insulin's action on target tissue, especially muscle and fat. This diabetogenic activity may result in an increase in the dose of insulin taken by the type I or type II diabetic patient. A GH antagonist may be used in this scenario to inhibit GH's diabetogenic activity, thereby increasing a patient's sensitivity to insulin. Thus, treatment of a diabetic patient with a GH antagonist could ultimately decrease the patient's insulin requirement.

While GHs have not previously been implicated in hypercholesterolemia, in another embodiment, the method of the invention is used to lower serum cholesterol levels.

It is expected that the GH antagonists of the invention can reverse the anti-insulin effects observed in both type I and type II diabetes patients and have substantial clinical effects on diabetic control in patients. In type I diabetics, a rise in the serum glucose levels in the early hours of the morning while the patient remains asleep (the "dawn phenomena") has been linked to a nocturnal rise in GH levels. Treatment with a GH antagonist is expected to abolish this effect, leading to more consistent control and lower fasting serum glucose levels. In type II diabetics, the principal cause of elevated fasting glucose levels is unrestrained hepatic glucose production ("HGP"). In normal, non-diabetic subjects insulin effectively suppresses HGP to modest levels throughout the night. Type II patients, with insulin resistance at the level of the liver as well as in peripheral tissue, have greatly increased HGP despite normal or higher than normal insulin levels. Given the effects of GH in raising HGP and intensifying the insulin resistance of type II diabetic patients, it is expected that antagonism of GH action with a GH antagonist will have a significant effect in lowering HGP, resulting in a decrease in fasting glucose levels.

In another embodiment, the method of the present invention is used to treat or prevent cancers, including but not limited to, lymphoblastic leukemia, melanoma, lymphoma, adenocarcinoma, colorectalcarcinoma and lung, breast, ovarian, pancreatic and prostate cancer. Specifically, the, methods of the invention involve administering a growth hormone antagonist together with a pharmaceutically acceptable carrier to reduce tumor load and/or reduce a pathological effect or symptom of the cancer. Additionally, such methods decrease the need (frequency) for and improve the efficacy of radiation therapy and chemotherapy and generally improve the quality of life.

In other embodiments, the GH antagonists of the invention are used in methods for treating vascular eye diseases to reduce a pathological effect or symptom of the disease and/or prevent the development or retard the progression of neovascularization as found, for example, in diabetic retinopathy, retinopathy of prematurity, retinopathy of sickle-cell anemia and age-related macular degeneration.

In yet another embodiment, a GH antagonist is used to prevent restenosis after coronary balloon angioplasty.

In another embodiment, the present invention is used to counter the adverse effects of endogenous GH or clinically administered GH. Adverse effects of endogenous GH include but are not limited to symptoms associated with acromegaly, gigantism, and diabetes mellitus. These symptoms have been described in detail in the section on BACKGROUND OF THE INVENTION.

The appended claims are hereby incorporated by reference as a further enumeration of the preferred embodiments. All patents and publications cited in this specification are incorporated by reference.

BRIEF DESCRIPTION OF THE DRAWINGS

FIG. 1 Amino acid sequence of bGH (G119R) and nucleotide sequence of the gene encoding this analogue. The alpha helices are marked and the amino acids are numbered, with number 1 being the first amino acid of the mature protein. The boldfaced bases and amino acids are those mutagenized in the G119R mutant.

The views were prepared by use of molecular modelling software (QUANTA and CHARMm, Ploygene, Waltham, Mass., USA).

Figure 9A:
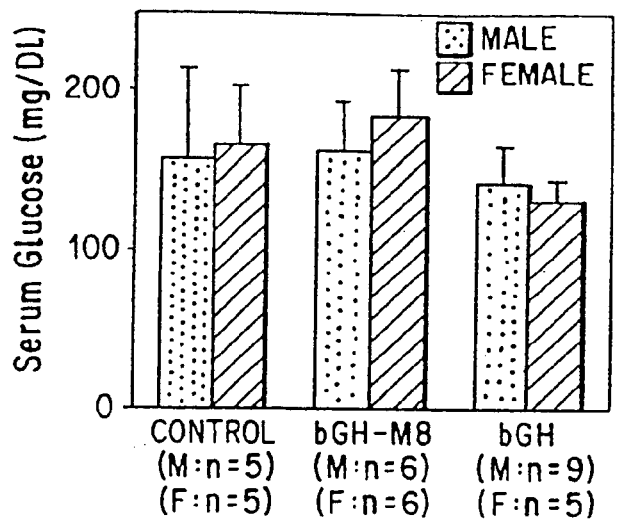
Figure 9B:
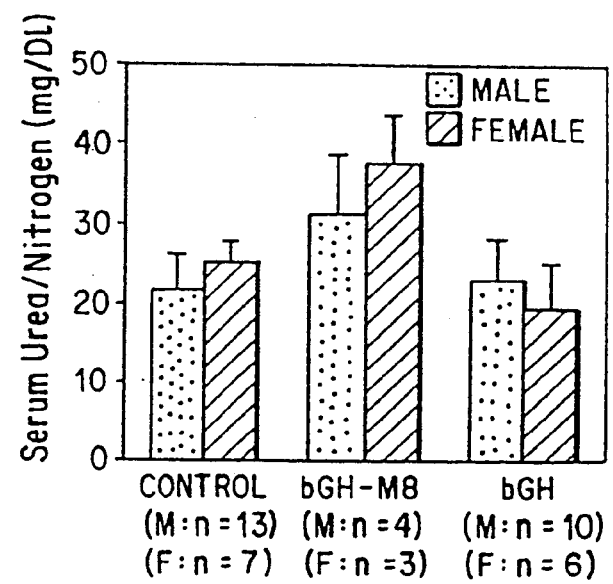
Figure 9C:
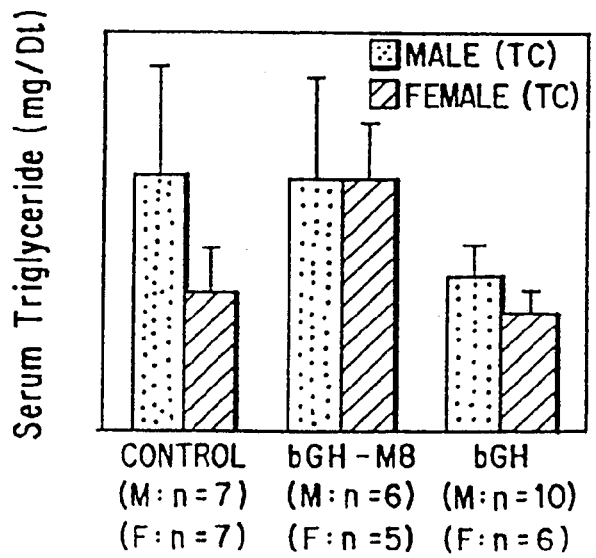

FIGS. 9A–9C compare serum glucose (FIG. 9A), urea/nitrogen (FIG. 9B), and triglyceride (FIG. 9C) levels of control mice, transgenic bGH-M8 (E117L,G119R,A112D)-producing mice, and transgenic wild-type bGH-producing mice, of both sexes.

Figure 10:
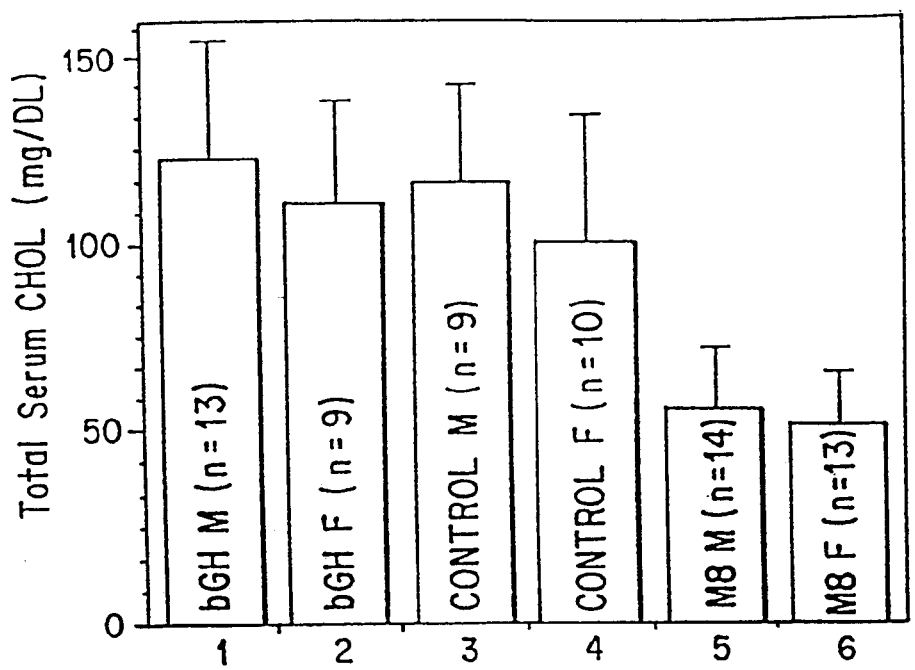

FIG. 10 compares serum cholesterol for transgenic wild-type bGH-producing mice, control mice, and transgenic bGH-M8-producing mice, of both sexes.

Figure 11:
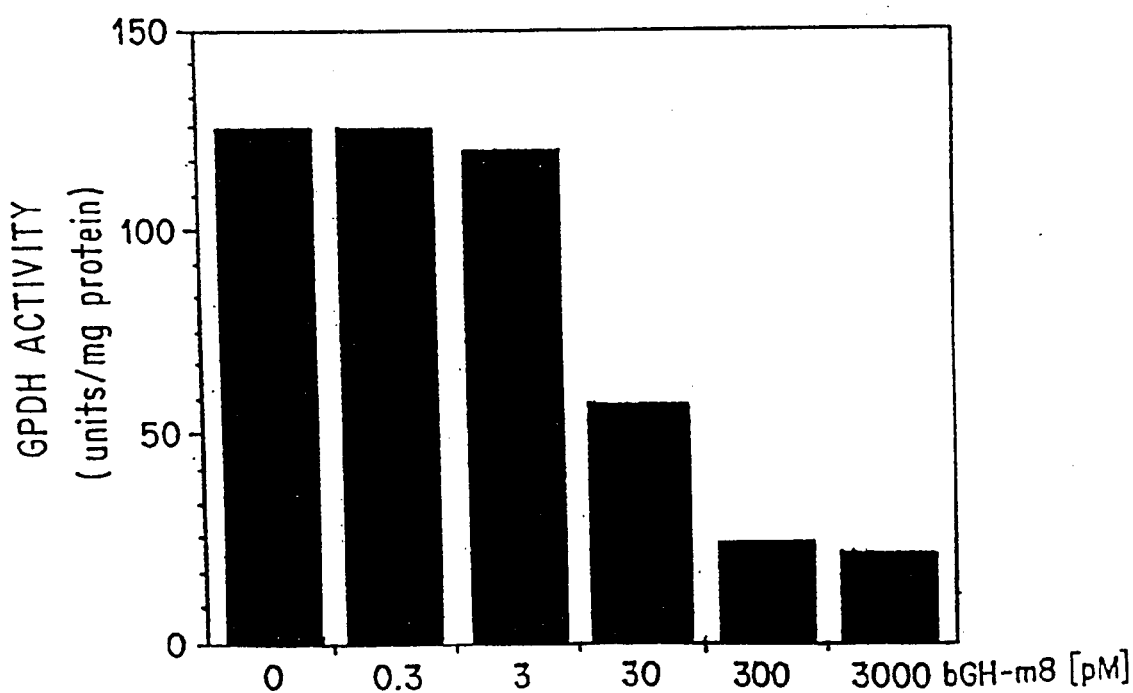

FIG. 11 plots glyceraldehyde-phosphate dehydrogenase ("GPDH") activity against bGH-M8 dosage in a competitive inhibition assay for the antagonism of the ability of GH (here, wild-type bGH) to promote the differentiation of preadipocytes (NIH 3T3-F442A cells).

Figure 12:
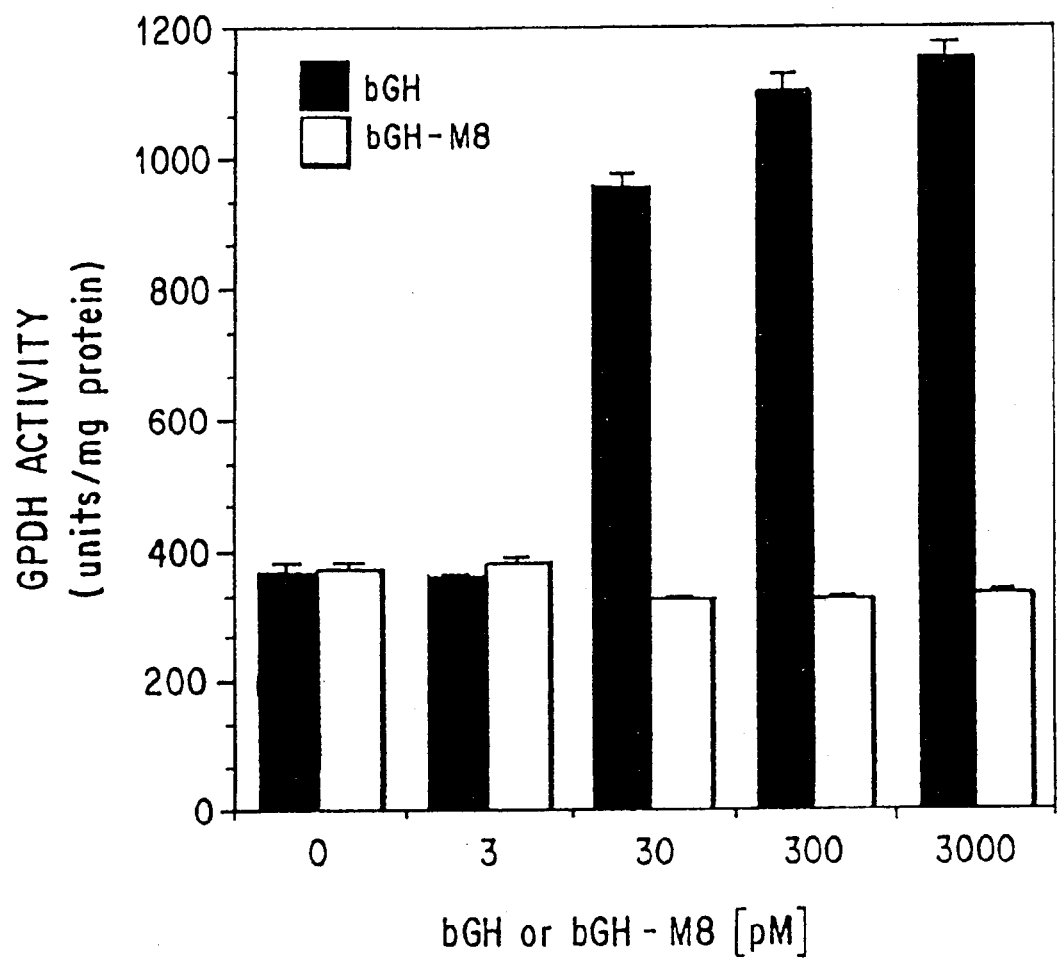

FIG. 12 compares effect of bGH and bGH-M8 on the differentiation of 3T3-F442A cells. At confluence, cells were incubated with increasing concentrations of bGH or bGH-M8. Cells were harvested on day 8 for determination of GPDH activity. The experiment was repeated twice with similar results. Each bar represents the mean value obtained from triplicate assays. The error bar represents the standard deviation.

Figure 13:
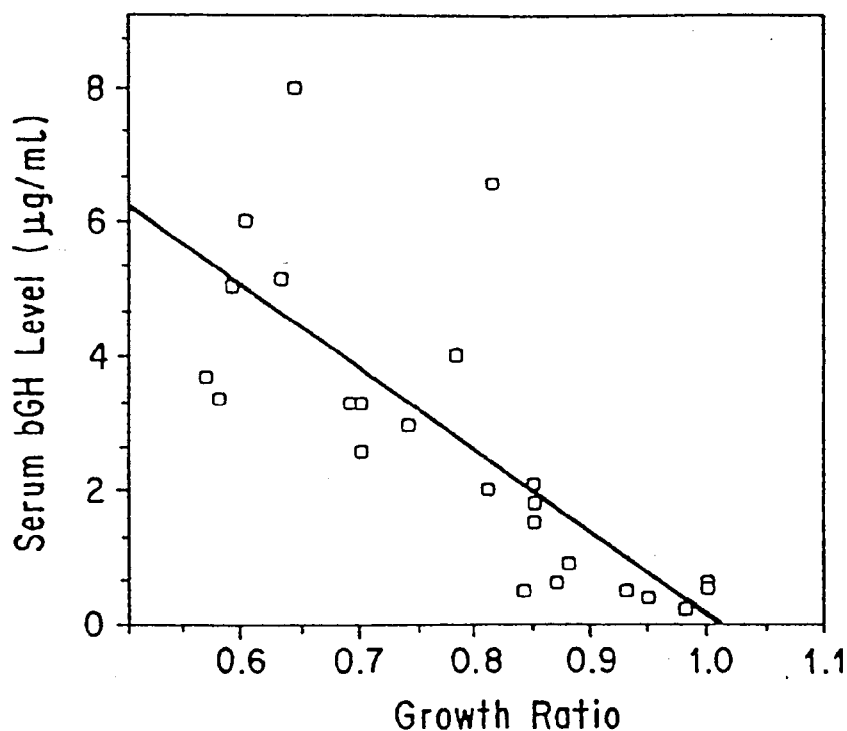

FIG. 13 shows the relationship between serum bGH analogue (G119R) concentrations and the growth ratio of transgenic mice/nontransgenic (TG/NTG). The ordinate represents bGH analogue (G119R) concentrations in serum. The abscissa represents the growth ratio of TG/NTG mice.

Figure 14:
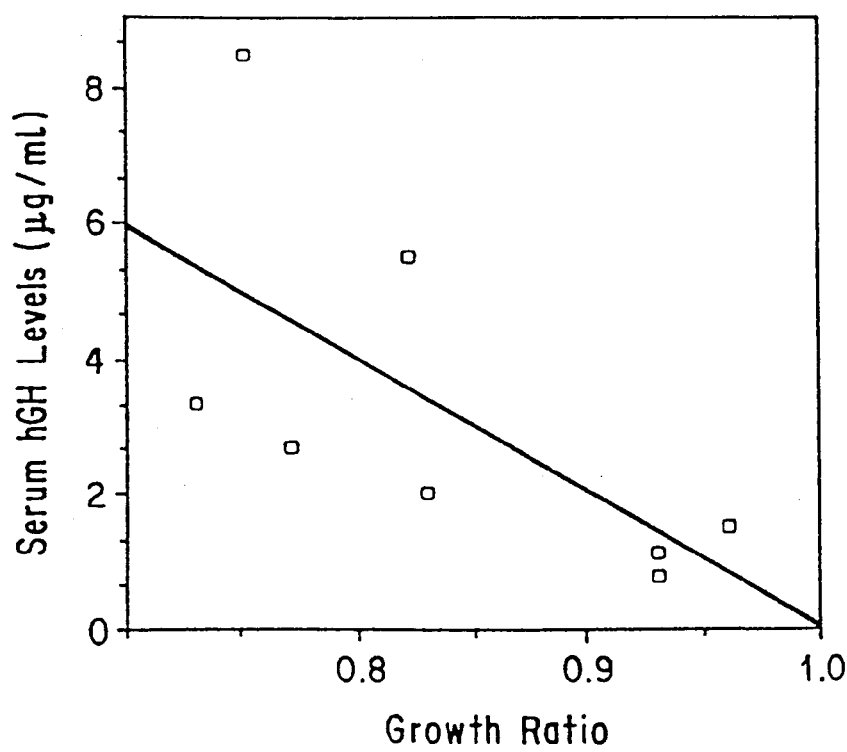

FIG. 14 shows the relationship between serum hGH analogue (G120R) concentrations and the growth ratio of TG/NTG.mice. The ordinate represents hGH analogue (G120R) concentrations in serum. The abscissa represents the growth ratio of TG/NTG mice.

DESCRIPTION OF THE PREFERRED EMBODIMENTS

The present invention relates to GH antagonists, especially growth inhibitors, which are peptides or proteins having a similarity in sequence and secondary structure to. vertebrate GHs, especially hGH and bGH.

The present invention also relates to methods of using such antagonists for treating diseases and disorders which are regulated wholly or partly by GHRs. Such diseases and disorders would include (a) those in which hGH action was excessive due to normal sensitivity of the tissues to increased levels of hGH (such as acromegaly and diabetes) and (b) those in which hGH action was excessive due to increased sensitivity of the tissues (as might result from increased GHR density) to normal levels of hGH (as in cancer and restenosis). However, other diseases and disorders, such as vascular eye diseases, might not be associated with either situation but might nonetheless be amenable to treatment with GH antagonists.

Preferably, the GH antagonist comprises an alpha helix having an amino acid sequence homology of a least about 50% with the third alpha helix of a vertebrate GH, especially bGH or hGH. Other alpha helices of the native hormone may be omitted if this can be done without loss of growth-inhibitory and/or other GH antagonist activity. The use of the term "antagonist" is in a functional sense and is not intended to limit the invention to compounds having a particular mechanism of action.

The overall percentage homology of bGH with other mammalian GHs is high: porcine (92%), ovine (99%), human (66%) and rat (87%). Insofar as the third alpha helix (amino acid sequence homologous to bGH 109–126) is concerned, the percentage homology is comparable to the overall figure: porcine (94%), ovine (94%), human (66%), and rat (94%).

The secondary structure of a polypeptide is a regular arrangement of a linear segment of the polypeptide chain. The most commonly encountered secondary structures are the beta-sheets and the alpha helices. See Schulz and Schimer, *Principles of Protein Structure* 69 (Springer-Verlag: 1979). The alpha helix is stabilized by hydrogen bonding between peptide amide and carbonyl groups of residues separated by a single turn of the helix. Secondary structure predictions are based on observation of the frequency of occurrence of the amino acid in a beta-sheet, alpha helix, etc., in a protein having a known three-dimensional structure.

The three-dimensional structure of porcine GH has been determined by X-ray diffraction and compared to that of other GHs. Abdel-Meguid et al., Proc. Natl. Acad. Sci. USA 84:6434 (1987). Like the other GHs thus studied, it is a single domain protein arranged as a four helix bundle with the helices in an antiparallel relationship. Its four helices are made up of residues 7–34, 75–87, 106–127 and 152–183. For X-ray studies of bGH and hGH, see Bell et al., J. Biol. Chem. 260:8520–25 (1985) and DeVos et al., Science 255:306–312 (1992). The three-dimensional structures of other GHs may be deduced by comparison of the sequences with due regard for the secondary structure.tendencies of substituted amino acids. Detailed structural models of GH may, in conjunction with the information provided in this application, be used by the person of ordinary skill in the art to introduce one or more mutations into GH antagonists without interfering with ability of a given GH antagonist to serve as a GH antagonist.

bGH is 92% homologous at the amino acid sequence level with porcine GH, and bGH's structure has been deduced by study of the two sequences and-of the structure of porcine GH. Its four alpha helices have been reported to be assumed by amino acids 4–33, 66–80, 108–127 and 150–179. The third alpha helix of bGH is defined as amino acids 106–129. However, it will be noted that the ends of this helix have a less marked alpha helical secondary structure than does the central region, which is 109–126. The exact bounds of the third alpha helix may differ for other GHs, depending on the alpha helical tendencies of "end" amino acids. The conformation is reasonably consistent with the predictions made by Chen and Sonenberg, Biochemistry 16:2110 (1977) using the method of Chou and Fasman, Biochemistry 13:222 (1974) (amino acids 10–34, 66 –87, 111–127, 186–191).

Figure 2:
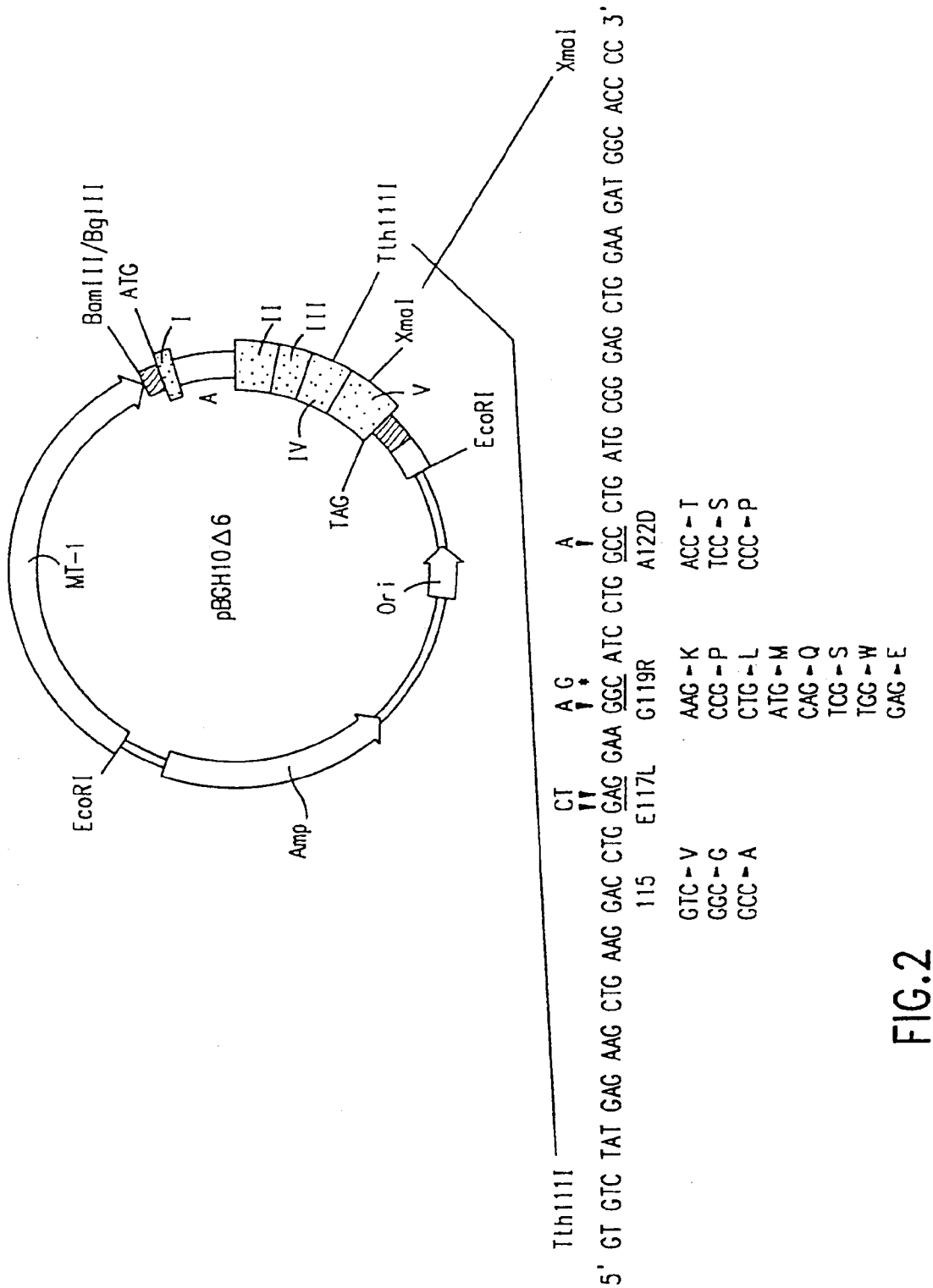
FIG. 2 General strategy of oligonucleotide directed mutagenesis. pBGH-10Δ6 was used as the parental vector. It contains mouse metallothionein I transcriptional regulatory sequences (MT-1) fused to the bGH gene (BamHI joined with BglII) which contains five exons (shaded boxes I–V) and intron A. This fusion gene was incorporated into pBR322 at the EcoRI site. The pBR322 origin of replication (ORI), ampicillin resistant gene (Amp), as well as the bGH translation start (ATG) and stop (TAG), codons are indicated. 5' and 3' non-translated regions are shown in hatching. The nucleotide sequence between restrictions sites Tth111I and XmaI is shown. Substitution mutations are indicated. One silent mutation is also indicated (*) which created a unique BamHI site. The position of the principal amino acid residues mutated in our experiments (115, 117, 119, 122) are indicated.
Figure 3:
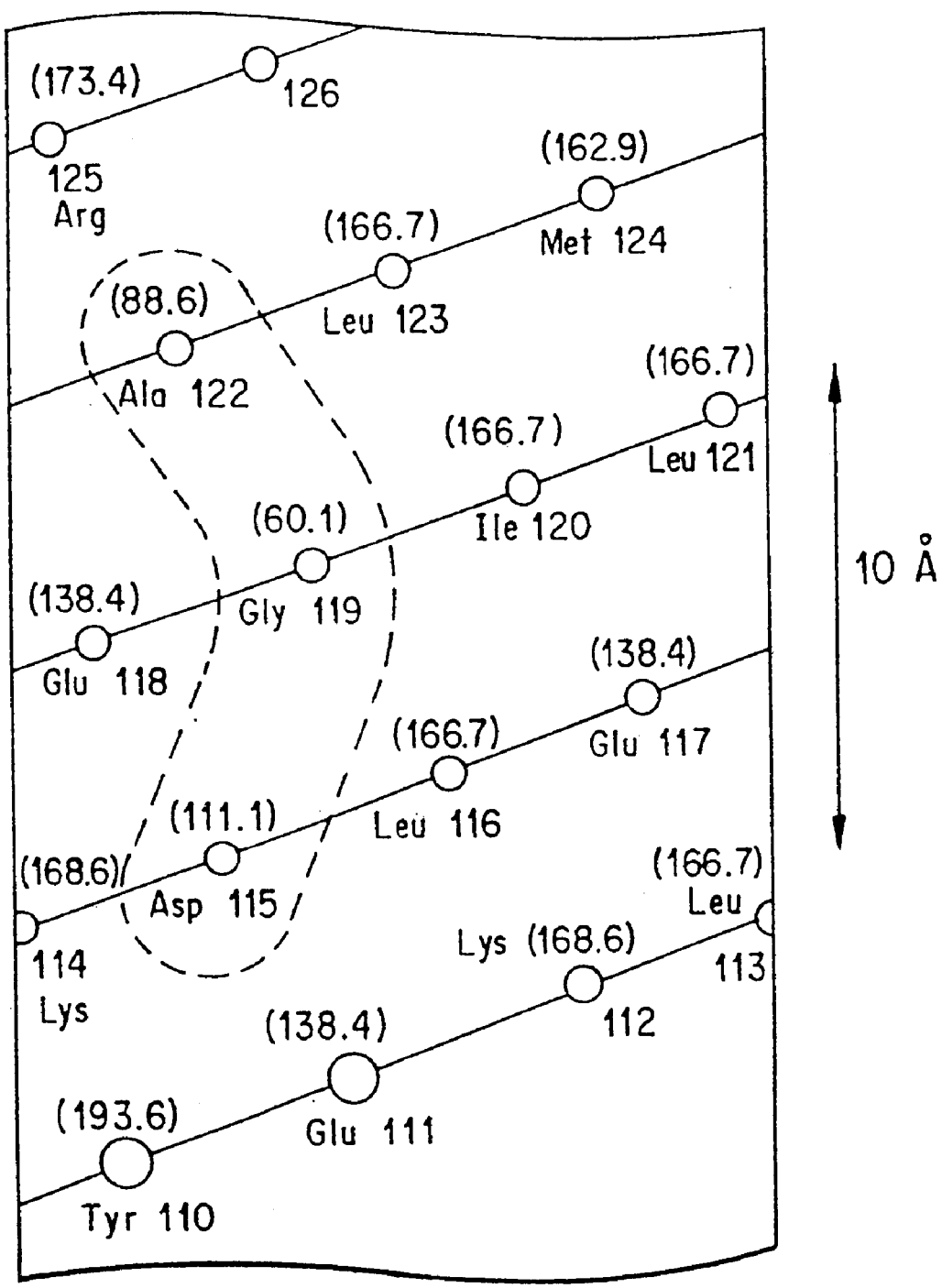
FIG. 3 is an idealized surface net (cylindrical plot) representation of most of the third alpha helix of bGH. The surface net is produced by projection of the helix onto a coaxial cylindrical sheet of paper, cutting this paper parallel to the helical axis and flattening it. The volumes of the amino acids are given in parenthesis. A dashed line indicates the cleft or depression formed by Ala122-Gly119-Asp115.
Figure 4:
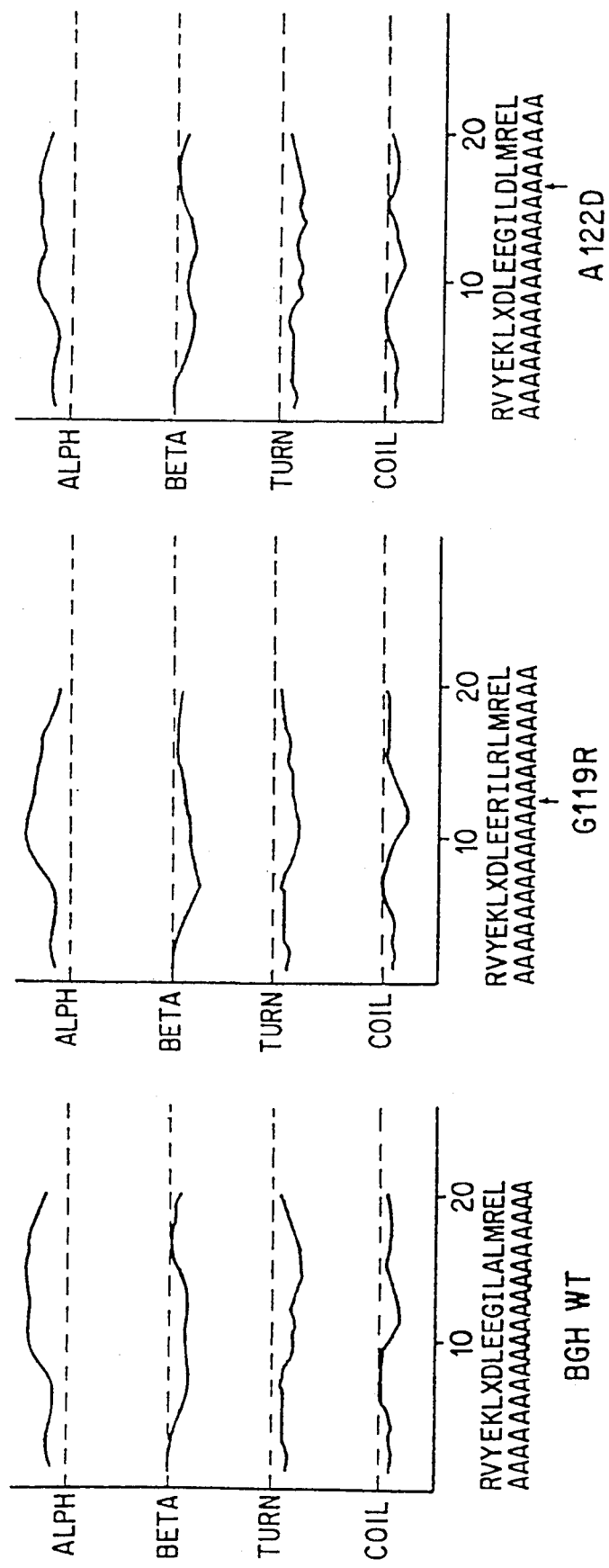
FIGS. 4A–4C are plots of the secondary structure prediction (alpha helix beta-sheet reverse turn, random coil) for amino acids 108–127 of wild-type bGH (FIG. 4A), bGH mutant G119R (FIG. 4B), and bGH mutant A112D (FIG. 4C). These plots were generated by the "Micro-Genie" program.

The amino acid sequences of the GHs isolated from various vertebrate species are highly conserved. In a comparison of flounder GH with other GHs, including bGH, Watahiki et al., J. Biol. Chem. 264:312 (1989), which is incorporated herein by reference, identified five conserved regions. Watahiki's conserved region GD4 comprises the stretch LKDLEEGILALMRELED of bGH, i.e., residues 113 to 129. Watahiki's FIG. 3; identifies residues conserved among the GHs and residues predicted to be important for the manifestation of growth-promoting activity.

Studying Watahiki's GD4 consensus region, several families of GHs may be discerned. The first family (I) comprises cGH, pGH, oGH; bGH, and hGH. These begin with LKDLEEG. They then continue with IQA (cGH, rGH, pGH), ILA (oGH, bGH) or IQT (hGH). All members of family I then conclude GH4 with LMRELED (except for rGH, LMQELED, and hGH, LMGRLED). The second family (II) comprises fGH, yGH, tGH and sGH. These have the consensus sequence LS (E/D) LK (M/T) G(L/I) (L/G/H/N) (K/L) LI (E/T/R/I) (A/G) (NIS) QD.

Five amino acids in GD4 are conserved among all of, the GHs noted by Watahiki: Leu-113, Leu-116, Gly-119, Leu-123 and Asp-129 (numbering according to the bGH sequence). Of the amino acids nearest Gly-119 on the face of the third alpha helix, Asp-115 is strongly conserved (replaced by Glu in the fish hormones); Leu-116 is invariant, Glu-118 is conserved among the mammals and birds, but replaced by Met, Thr or Val in fish; Ile-120 is almost invariant (replaced by Leu in fGH), and Ala-122 is well conserved, especially in mammals and birds (replaced by Thr in hGH and Leu or Lys in fish GHs). (It should be understood that the present invention is not limited to mutants in which these conservations are maintained).

It has been shown that a recombinant molecule containing a hGH (1–134) fragment linked to a human placental lactogen (141–191) fragment retained full hGH immunological activity and binding affinity to GH receptors isolated from rabbit liver. Russell et al., J. Biol. Chem. 256:296–300 (1981). By using the homolog-scanning mutagenesis technique, gene fragments of homologous hormones, i.e., human placental lactogen or human prolactin, were systematically substituted throughout the hGH gene, thus producing various chimeric hormones. Cunningham et al., Science 243:1330–36 (1989). A comparison of the binding affinities of these mutant GHs and wild-type hGH to a cloned liver human GHR led to the conclusion that there were three discontinuous polypeptide determinants in hGH involved in receptor binding. They were located at the amino-terminus, carboxy-terminus, and within a loop between amino acid residues 54and 74. These putative binding domains were further analyzed by an alanine-scanning mutagenesis technique in which alanine residues were systematically substituted throughout those regions. Amino acid residues at positions 10, 58, 64, 68, 172, 174, 175 and 176 of hGH were shown to be important for GH receptor binding. However, none of the mutant GHs were reported to inhibit growth. Cunningham et al., Science 244:1081–85 (1989).

The present invention is not limited to the mutation of the third alpha helix of bGH or hGH. Rather, it encompasses the mutation of the third alpha helix of any mammalian or other vertebrate GH, including, but not limited to, the GHs whose sequences are given in Watahiki (1989): flounder, yellowtail, tuna, salmon, chicken, rat, porcine, ovine, bovine and human GHs. Expression of mutants of other GHs is facilitated by the availability of genes encoding the latter. See, e.g., Goeddel et al., Nature 281:544–548 (1979). In addition, the present invention is not limited to muteins of mammalian or vertebrate GHs comprising mutations only within the third alpha helix, but also encompasses muteins having mutations outside the third alpha helix in addition to those mutations within the third alpha helix such that the muteins-exhibit GH antagonist activity.

The concept of a polypeptide which is substantially homologous to bGH is deemed to include (but is not limited to) any polypeptide which differs from bGH or hGH by (a) a substitution (or deletion) at an amino acid corresponding to amino acids 115 to 119 of bGH, (b) a substitution (or deletion) at an amino acid corresponding to an amino acid of bGH or hGH which is not conserved among the vertebrate GHs, especially the replacement of that amino acid by one found at the site in a different GH, and/or (c) truncation of amino acids 1–95 and/or 134–191. (Conserved amino acids are identified in Watahiki et al., 1979). Thus, all non-bovine vertebrate GHs are "substantially homologous" with bGH and/or hGH. Preferably, the polypeptide is a least about 50% homologous, more preferably at least 80% homologous, with bGH or hGH in the subsequence substantially corresponding to the third alpha helix (approximately, residues 106–129) of bGH, and more preferably over the entire length of the polypeptide (ignoring extraneous non-bGH-related fusions to the amino-terminus or carboxy-terminus).

The compound is considered to be growth-inhibitory if the growth of test animals of at least one vertebrate, species which are treated with the compound (or which have been genetically engineered to express it themselves) is significantly (at a 0.95 confidence level) depressed with respect to the growth of control animals (the term "significant" being used in its statistical sense). Preferably, it is growth-inhibitory in a plurality of species, or at least in humans and/or bovines. GHs have considerable interspecies cross-reactivity. Gill et al., Biotechnology 3:643 (1985) reported that recombinant chicken and bovine GHs accelerate growth in juvenile pacific salmon.

It is known that certain fragments of GHs also have growth-promoting activity, and it is expected that the growth-inhibitory peptides (the term "peptides" is used herein to include proteins) of the present invention need not be as large as bGH. Preferably, the peptides are at least 11 amino acids long (three turns of an alphahelix) and more preferably at least 50 amino-acids long. These peptides may retain the growth-inhibiting action of, e.g., bGH (G119R), yet lack other, undesirable biological activities of the native size mutant. They may also have more desirable pharmacokinetic characteristics.

The growth-inhibitory peptides of the present invention may also be larger than bGH, provided that the additional amino acids-do not result in the compound being unable to reduce the growth rate of a vertebrate.

While the mechanism of action of the growth-inhibitory peptides is not known, it is believed that they function as antagonists;to wild-type GHs endogenously produced by the target animal We have shown that, e.g., bGH (G119R) and bGH (G119R,E117L,A122D), both competitively inhibit the binding of wild-type bGH to liver membrane preparations. Thus, it is believed that the compound has a net result of inhibiting growth because its growth-promoting, activity is substantially less than that of wild-type GHs (and perhaps is negligible), yet it can displace from GHR sites the endogenous native GH (whose stimulation of growth would have been more.pronounced). However, applicants are not bound by this theory.

Figure 5:
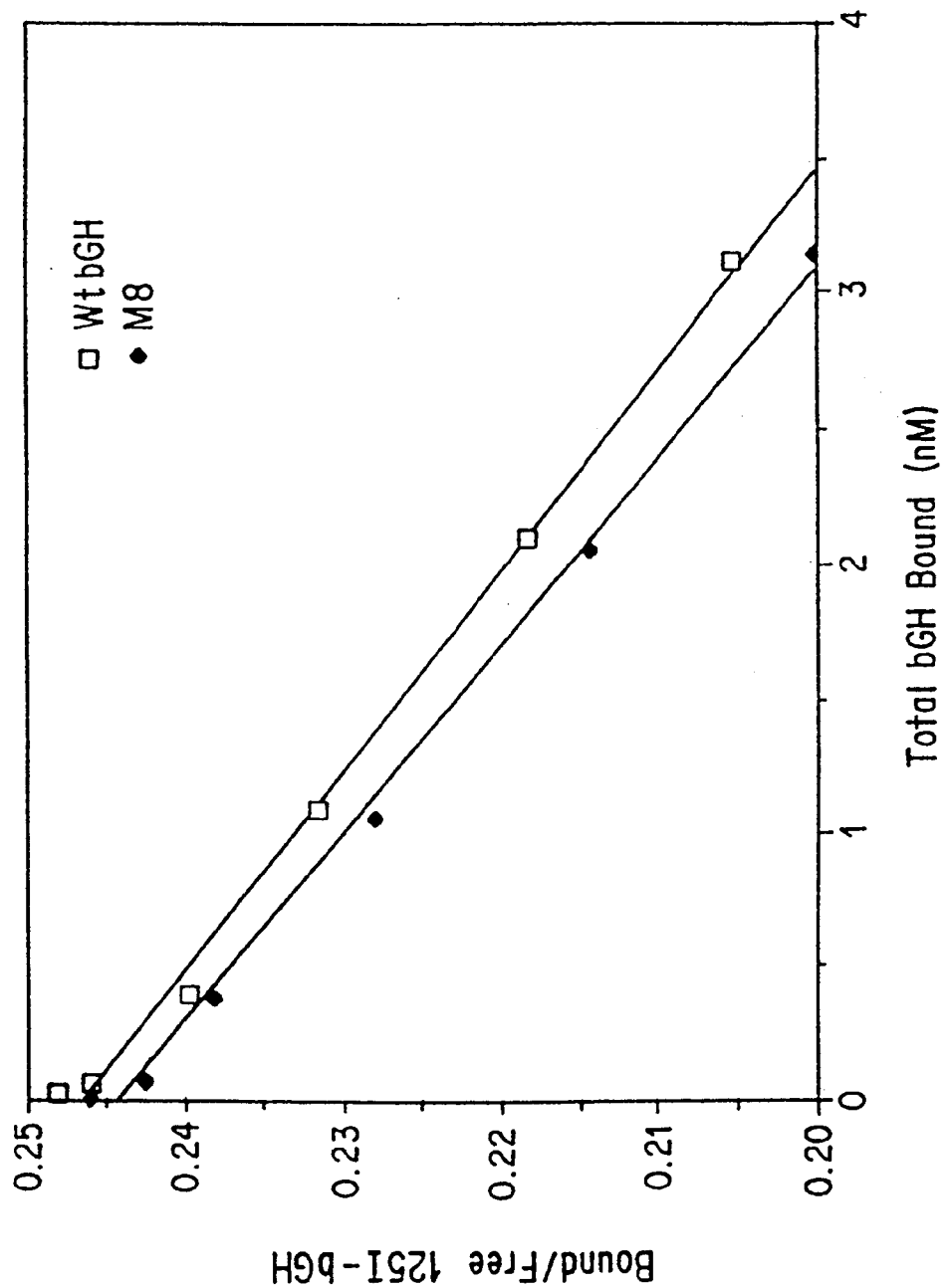
FIG. 5 Scatchard plots of data from competitive binding experiments for wild-type bGH and bGH-M8 using mouse liver membrane preparations. The ordinate represents the, ratio of bound to free bGH and the abscissa the concentration of total bGH bound. Each point represents the mean of four experiments which were carried out in triplicate.
Figure 6:
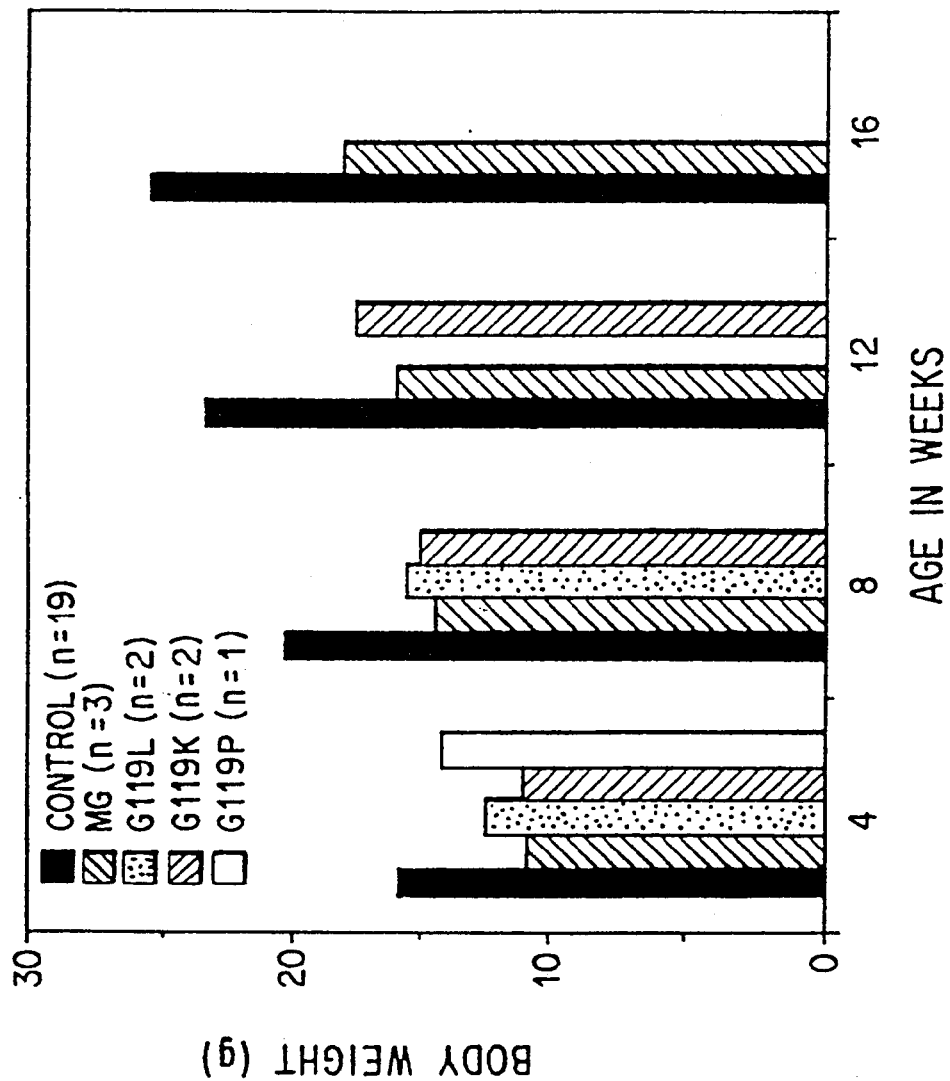
FIG. 6 provides a growth rate comparison among control (nontransgenic), G119R, G119L, G119K and G119P mice, illustrating the growth-inhibitory effect on these mutants.
Figure 7:
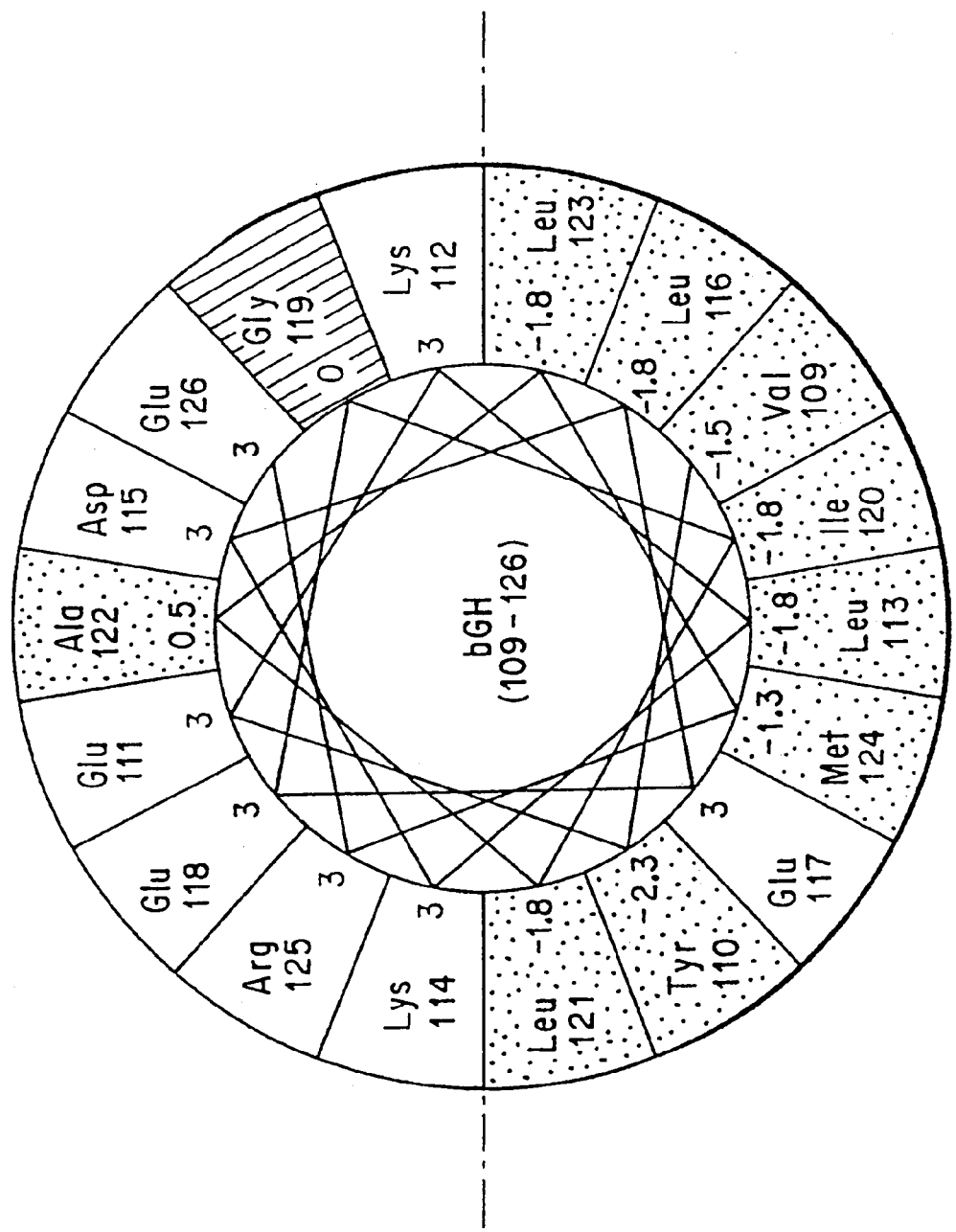
FIG. 7 presents an axial view of the third alpha helix (109–126) of bGH, showing its amphipathic tendencies. Hydrophobic amino acid sectors are shaded by dots; hydrophilic amino acids are indicated by open sectors; the Gly sector, a neutral amino acid, by slanted lines. The residue numbers and hydophilicity values (Hopp and Wood scale) are given.
Figure 8B:
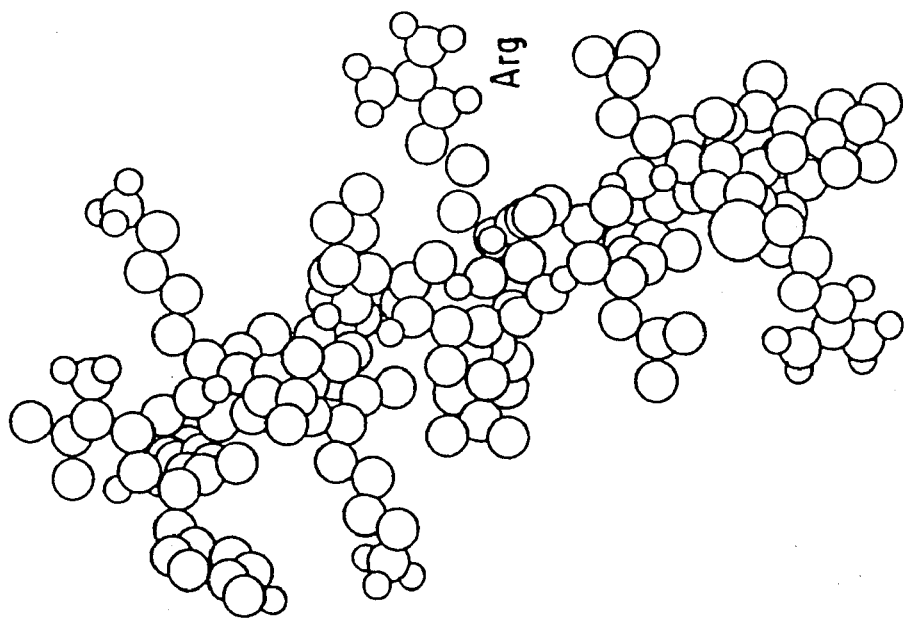
FIGS. 8A–8B present side views of the third alpha helix of wild type (FIG. 8A) and G119R mutant (FIG. 8B) bGHs projected on the plane in which the side chain of the Arg-119 of the mutant G119R lies. The Gly-119 residue found at the bottom of the cleft is indicated by an arrow.
Figure 8A:
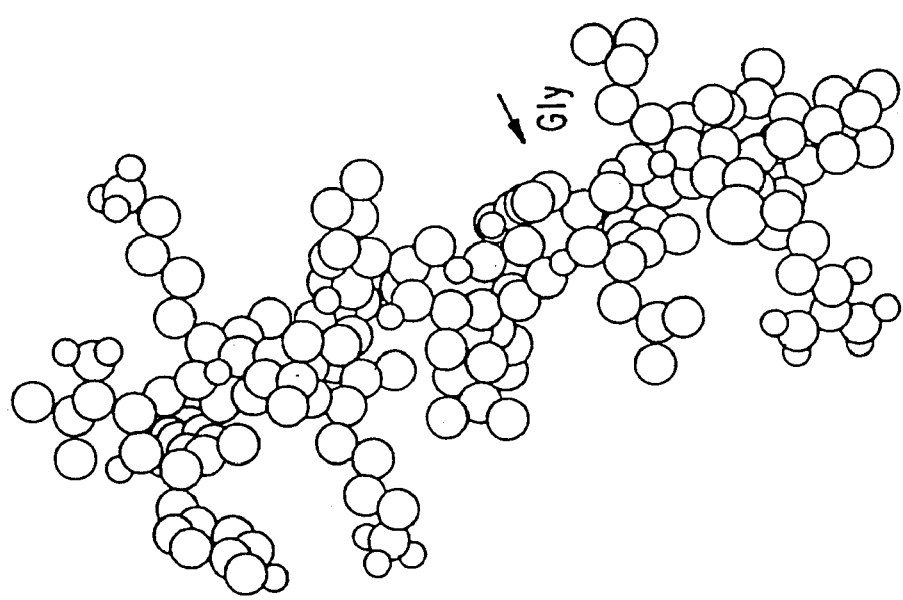

DeVos et al., Science 255:306 (1992) examined the complex of hGH and the extradellular domain of its receptor by X-ray diffraction. The first receptor-binding region of hGH is concave and is formed mainly by residues on exposed faces of helix 4, but also by exposed residues of helix 1 and residues in the region connecting helices 1 and 2. The second receptor-binding region comprises the exposed sides of helices1 and 3 and is relatively flat. The role of helix 3 is shown best in DeVos' FIG. 5; there is a significant decrease in solvent accessibility around hGH E119 upon complex formation. The complex had the form hGH-(hGHR)$_2$; that is, the receptor dimerizes to interact with hGH. It is possible that our GH antagonists interfere with this dimerization.

Preferably, the compounds of the present invention have an ED50 which is less than about 10 times the ED50 of wild-type bGH in an assay of the ability of the compound to displace radiolabeled wild-type bGH from a liver membrane preparation made as described below. More preferably, the compounds have an ED50 at least comparable to that of wild-type bGH. Most preferably, the compounds have a higher affinity for GHRs than does the GH native to the animal receiving the compound. For purification and characterization of a human GHR see Leung et al., Nature 330:537–43 (1987)

A GH mutein may be considered an antagonist, even if it lacks growth-inhibitory activity, if it antagonizes another GH-mediated.activity, e.g., diabetogenic, glomerulosclerotic, hypercholesterolemic, tumorigenic or retinopathic activities.

The preferred growth-inhibitory peptides are characterized by a modification of the surface topography of the third alpha helix. It will be seen from FIG. 3 that in the third alpha helix of "wild-type" bGH, there is a surface cleft or depression beginning at the Asp-115, deepening at the Gly-119, and ending with the Ala-122. All of the mutants prepared so far, both those which retain the wild-type growth-promoting activity and those which do not, are consistent with the theory that growth-promoting activity requires the presence of this cleft or depression and that, if the center of this cleft is "filled in" by substitution of amino acids with bulkier side chains, the mutein inhibits the growth of the subject.

Mutations which substantially destabilize the alpha helix are undesirable since they may result in the loss of all growth-related activity. We have observed such loss in the case of several mutations which were expected to disrupt the alpha helix.

For a discussion of alpha helix formers and breakers, see Chou and Fasman, supra. Glu, Ala and Leu are the preferred alpha helix formers while Pro and Gly are characterized as strong helix breakers. Substitutions which introduce strong alpha helix breakers are less desirable, but may be tolerated in a particular case, such as at the end of the helix. The secondary structures of our analogues have been predicted using the "Micro Genie" computer program, which uses the algorithm of Ganier et al., J. Biol. Chem. 120:97–120 (1978).

With respect to amino acid 119, Gly is both the smallest amino acid residue and the one least favorable to alpha helix formation. Thus, it is believed that any other amino acid may be substituted for it without destabilizing the alpha helix, while at the same time filling in the aforementioned cleft. Alternatively, the replacement amino acid may be chemically modified to have a chemical moiety that effectively "fills" the cleft, e.g., an amino acid such as lysine that has been chemically substituted with polyethylene glycol (see the discussion below). All of the G119 bGH substitutions tested resulted in a "small animal" phenotype. These substitutions were Arg (a large, aromatic amino acid), Pro (a cyclic aliphatic amino acid), Lys (a large, positively charged amino acid), Trp (a large aromatic amino acid) and Leu (a large, nonpiolar, aliphatic amino acid). In hGH, the homologous Gly is at position 120. Substitution of Arg or Trp resulted in an antagonist, however, hGH G120A retained growth-promoting activity. Consequently, it is presently believed that this Gly, which is conserved in all vertebrate GHs, may be replaced by any amino acid other than Ala (the second smallest amino acid), and more preferably by any amino acid which is at least as large as Pro (the smallest replacement amino acid known to result in a "small" animal phenotype). The deletion of bGH Gly-119 and hGH Gly-120-is also known to result in a "small" animal phenotype and would be a GH antagonist.

Modification of position bis suggested by our "cleft" theory. The Asp at position 115 may be replaced by a bulkier amino acid which does not destroy the alpha helix. Preferably, the replacement amino acid has a size greater than that of Asp. The amino acids His, Met, Ile, Leu, Lys, Arg, Phe, Tyr and Trp are substantially larger than Asp. Of these, His, Met, Leu and Trp are more preferred because they combine the advantages of bulk with a reasonably strong alpha-helical propensity. Note, however, that Glu is the strongest alpha helix former of all of the amino acids. The D115A mutant of bGH is not a GH antagonist, but Ala is smaller than Asp, so this is not probative of the value of replacing Asp-115 with a bulkier amino acid.

It is possible that G119A might lead to a "small" phenotype if coupled with other mutations, e.g., at positions 115 and 112.

It is possible to systemically screen for the effect of all possible amino acid substitutions at positions 115 and 119. (There are $20^2-1$ or 399 combinatorial possibilities). DNA which encodes bGH and is degenerate at these positions, so as to encode all possible amino acids, or only those with acceptable alpha-helical propensities, is prepared, e.g., by a "dirty bottle" synthesis. Phage are prepared, as taught by Ladner et al., PCT/US89/03731; WO90/02809, which display the mutant bGHs as a domain of a chimeric coat protein. The phage are incubated with a chromatographic support bearing a GHR. (For the techniques of isolating GHRs, see Leung et al., Nature 330:537 (1987) and Spencer et al., J. .Biol. Chem. 263:7862 (1988).) Native bGH is also incubated with the support, before, during or after the phage incubation. Bound phage are recovered, amplified and examined to determine the sequence of the mutant bGH (usually by sequencing the corresponding gene in the phage genome). These mutants have demonstrated the ability to compete with wild-type bGH for a GHR. Their ability to antagonize GH activity in vivo is then confirmed by, e.g., administering them directly to an animal or by preparing a suitable transgenic animal, or by the in vitro assay described in Example 7. This approach may be extended, if desired, to other amino acid positions in the third alpha helix. Amino acids which are particularly preferred for screening are the six amino acids spatially nearest bGH's Gly-119, that is, Ala-122, Leu-123, Ile-120, Leu-116, Asp-115 and Glu-118. It should be noted that Bass et al., Proteins: Structure, Function and Genetics, 8:309–314 (1990) prepared "hormone phage" which express and display hGH-geneIII fusion proteins and which were bound by anti-hGH monoclonal antibodies. Moreover, it was possible to separate phage bearing wild-type hGH from phage bearing the low affinity hGH mutant R64A by means of affinity chromatography (using the extracellular domain of the hGH receptor bound to nonporous oxirane beads).

Besides the mutations at position 119, which is deemed necessary to impart the desired growth-inhibitory activity, additional mutations are possible which will leave the growth-inhibitory activity or other antagonist activity intact. These mutations may take the form of single or multiple substitutions, deletions, or insertions, in nonessential regions of the polypeptide. For example, it is possible to alter another amino acid in the alpha helix provided that the substitution does not destroy the alpha helix. Preferably, such alterations replace an amino acid with one of similar size and polarity. It may be advantageous to modify amino acids flanking the primary mutation site 119 in order to increase the alpha-helical propensities of the sequence, particularly if the mutation at position 119 is one expected to destabilize the helix.

The following table may be helpful in identifying candidate mutants:

| Amino Acid | Volume (angstroms) | Alpha Helicity |
|---|---|---|
| Gly(G) | 60.1 | 0.53 |
| Ala(A) | 88.6 | 1.45 |
| Ser(S) | 89.0 | 0.79 |
| Cys(C) | 108.5 | 0.77 |
| Asp(D) | 111.1 | 0.98 |
| Thr(T) | 116.1 | 0.82 |
| Asn(N) | 117.7 | 0.73 |
| Pro(P) | 122.7 | 0.59 |
| Glu(E) | 138.4 | 1.53 |
| Val(V) | 140.0 | 1.14 |
| Gln(Q) | 143.9 | 1.17 |
| His(H) | 153.2 | 1.24 |
| Met(M) | 162.9 | 1.20 |
| Ile(I) | 166.7 | 1.00 |
| Leu(L) | 166.7 | 1.34 |
| Lys(K) | 168.6 | 1.07 |
| Arg(R) | 173.4 | 0.79 |
| Phe(F) | 189.9 | 1.12 |
| Tyr(Y) | 193.6 | 0.61 |
| Trp(W) | 227.8 | 1.14 |

In addition to any mutations in the third alpha helix that are deemed necessary to impart the desired growth-inhibitory activity, additional mutations are possible outside of the third alpha helix that will leave the growth-inhibitory activity or other antagonist activity intact. These additional mutations may take the form of single or multiple substitutions, deletions, or insertions, in regions of the polypeptide outside of the third alpha helix. For example, the invention encompasses a polypeptide having the amino acid sequence of a vertebrate GH in which an amino acid corresponding to Gly-119 of bGH is deleted or substituted with an amino acid, and in which at least one other position outside the third alpha helix of the polypeptide is deleted or substituted with an amino acid, as long as the resulting polypeptide retains GH antagonist activity. The mutation outside the third alpha helix may be anywhere that does not result in loss of GH antagonist activity. Preferably, such mutation outside the third alpha helix should be at a position corresponding to a non-conserved amino acid of a vertebrate GH. However, as described below, mutations at conserved amino acid positions, if carefully chosen, may be tolerated. More preferably, the mutation at a non-conserved amino acid position outside the third alpha helix should be at a position corresponding to a non-essential region of a vertebrate GH.

Several of the cited references provide guidance as to where and where not the polypeptide will tolerate mutagenesis. Watahiki-et-al. (1989) compared the sequence of flounder, yellowtail, tuna, salmon, chicken, rat, porcine, ovine, bovine and human GHs. They identified five conserved domains which were labeled GD1–GD5. Mutations in these conserved domains are more likely to affect-activity; GD4 corresponds to the third alpha helix of bGH. In mutating a known GH antagonist with the desire to retain inhibitory activity, mutations outside the conserved domains are more prudent. However, mutations in these conserved regions, if carefully chosen, may be tolerated; for example, the mutation E117L does not modify the activity of either wild-type bGH or a bGH-G119R mutant. Note that not only substitutions, but also insertions and deletions, are suggested by the example of the cognate hormones.

Abdel-Meguid et al. (1987) determined the three-dimensional structure of recombinant methionyl porcine GH, and suggested that it revealed the "general three-dimensional fold" of the GHs. The three-dimensional structure can be used to identify interior and surface residues; generally speaking, proteins mutated at surface residues (other than the receptor binding: site) are more likely to remain functional. However, Creighton and Chothia, Nature 339:14 (1989) discuss the toleration of mutations at buried residues. The structure may also be used to determine flexible surface "loops"; proteins are more tolerant of deletions and insertions in such regions.

Cunningham et al. (1989) used homolog-scanning mutagenesis to identify the epitopes of hGH for its cloned liver receptor. Only variant hormones having mutations in regions C(54–74), F(164–190), and, to a lesser extent, A(11–33), exhibited reduced binding affinity. Cunningham and Wells, Science 244:1081 (1989) used a related technique, alanine-scanning mutagenesis, to further study these regions. Note, however, that binding to the receptor utilized by Cunningham is not necessarily critical to the growth-promoting or growth-inhibitory activity of the mutant.

For example, it seems likely that major amino-terminal and carboxy-terminal truncations can be made without adverse effects on growth-inhibitory activity, since the 96–133 fragment of bGH (K112L) is understood to retain bioactivity. Truncations may be generated by gene modifications or by peptidase treatment.

In terms of the kinds of substitutions which may be made, one may look first to analyses of the frequencies of amino acid changes between homologous proteins of different organisms, such as those presented in Table 1–2 of Schulz and Schimer, supra and FIGS. 3–9 of Creighton, supra. Based on such analyses, we define conservative substitutions as exchanges within the groups set forth below:

| I | small aliphatic, nonpolar or slightly polar residues - Ala, Ser, Thr, (Pro), (Gly) |
| II | negatively charged residues and their amides - Asn, Asp, Glu, Gln |
| III | positively charged residues - His, Arg, Lys |
| IV | large aliphatic nonpolar residues - Met, Ile, Leu, Val, (Cys) |
| V | large aromatic residues - Phe, Tyr, Trp |

Three residues are parenthesized because of their special roles in protein architecture. Gly is the only residue without a side chain and therefore imparts flexibility to the chain. Pro has an unusual geometry which tightly constrains the chain. Cys can participate in disulfide bonds which hold proteins into a particular folding; the four Cysteines of bGH are highly conserved. Note that Schulz and Schimer would merge I and II above. Note also that Tyr, because of its hydrogen bonding potential, has some kinship with Ser, Thr, etc.

Within the GH family itself, we see a wide variety of substitutions of other amino acids for the residues of bGH. For example, among the vertebrate GHs set forth in Watahiki et al., (1989), Pro appears 6 times in bGH. The first Pro is not substituted, but is absent from sGH. The second is replaced by Leu in fGH; Thr in yGH and tGH. The third is replaced by Leu in fGH, Ile in yGH and tGH, Val in sGH. The fourth Pro is conserved. The fifth Pro is replaced by Phe in fGH;. Ser in yGH. The Sixth Pro is replaced by Phe in fGH, yGH and tGH, and Leu in sGH. Overall, Pro is replaced 4 times-by.Phe, 3 times by Leu, 2 times each by Thr and Ile, and once each by Val and Ser. When this analysis is extended to all amino acids of bGH, we obtain the following tallies:

Ala (14; 2 conserved)→Thr (14), Ser (11), Asp (7), Ile (4), Glu (4), Gly (4), Val (3), Gln (3), Leu (3), Lys (2), Phe (1), Asn (1)

Asp (10; 2 conserved)→Tyr (6), Asn (4), Val (4), Glu (3), Lys (2), Arg (2), Gly (2), Thr (1), Ser (1), Phe (1), Ala (1)

Glu (13; 2 conserved)→Asp (14), Lys (10), Gln (4), Ala (3), Pro (2), Thr (2), Asn (1), .Ser (1), Val (1), Met (1), Arg (1), Gly (1)

Phe (13; 3 conserved)→Tyr (7), Leu (6), Asn (6), Ser (5), Gln (3), Ile (2), Gly (2), His. (1), Thr (1), Val (1)

Gly (10; 1 conserved)→Arg (9), Glu (8), Asp (7), Val (4), Pro (4), Ser (4) Asn (3), Phe (3), Asp (2), His (1), Thr (1), Tyr (1), Ala (1)

His (3; 1 conserved)→Arg (1), Asn (1), Tyr (1), Asp (1)

Ile (7)→Gln (7), Asn (5), Leu (4), Phe (4), Val (4), Ala (2), Ser (1), Arg (1)

Lys (12; 2 conserved)→Ser (11), Arg (7), Gly (4), Gln (2), Leu (2), Asn (1)

Leu (27; 11 conserved)→Ser (11), Val (9), Asn (7), Met (7), Gln (7), Arg (4), Glu (4), Phe(3), Tyr (3), Gly (1), Pro (1), His (1)

Met (4)→Ile. (7), Ala (4), Thr (3), Ser (3), Leu (1), Asn (1), Val. (1)

Asn (6)→Ile (8), His (4), Asp (3), Gln (3), Glu (2), Ser (1)

Pro (6; 1 conserved)→Phe (4), Leu (3), Thr (2), Ile (2), Val (1), Ser (1)

Gln (11; 1 conserved)→Leu (13), Arg (6), Lys (5), Ser (4), Glu (4), His (1), Gly (l), Asp (l), Pro (1)

Arg (13; 1 conserved)→Lys (11), Ser (9), Thr (7), Ile (3), Glu (2), Gly (2), Asn (2), His (2), Val (1), Gln (1), Asp (1), Ala (1)

Ser (13; 3 conserved)→Ala (8), Asn (8), Gln (4), Leu (4), Gly (3), Glu (2), Asp (2), Thr (2), Arg (1), Val (1)

Thr (12; 1 conserved)→Ser (14), Ala (13), Val (7), Tyr (5), Phe (4), Ile (4), Met (3), Leu (3), Pro (2), Asn (2), Gly (1)

Val (6)→Ala (4), Ser (4), Ile (3), Thr (2), Gln (6), Gly (2), Met (2), Leu (l), Lys (1)

Tyr (6)→Leu (5), Pro (4), Gln (3), Phe (2), Glu (1), Ser (1)

Note that the above figures are not normalized to adjust for the relative frequencies of occurrence of the various amino acids. We further note that in our own mutagenesis experiments, changing Lys-112 to Leu or Lys-114 to Trp (M1), Glu to Gly (E126G) or Leu (M4), or Ala to Thr (A122T) did not alter activity, while changing Lys, Glu or Leu to Pro abolished.activity.

The subject invention also provides for various GH antagonist conjugates. The GH antagonists conjugates of the invention comprise a GH antagonist described herein (and in U.S. Pat. No. 5,350,836) covalently linked one or more water soluble polymers. Water soluble polymers, especially polyethylene glycol, have been conjugated to proteins so as to provide additional desirable properties while retaining, at least in part, the GH antagonist properties of the GH antagonist. These desirable properties include increased solubility in aqueous solutions, increased stability in storage, reduced immunogenicity, increased resistance to proteolytic degradation, and increased in vivo half-life. Water soluble polymers suitable for use in the subject GH antagonists include polyethylene glycol homopolymers, polypropylene glycol homopolymers, copolymers of ethylene glycol with propylene glycol, wherein said homopolymers and copolymers are unsubstituted or substituted atone end with an alkyl group, polyoxethylated polyols, polyvinyl alcohol, polysaccharides, polyvinylethyl ethers, and α,μ-poly [(2-hydroxyethyl)-DL-aspartamide]. Polyethylene glycol is particularly preferred. Methods of making water-soluble polymer conjugates of proteins are described in, among other places, U.S. Pat. No. 4,179,337; U.S. Pat. No. 4,609, 546; U.S. Pat. No. 4,2:61,973; U.S. Pat. No. 4,055,635; U.S. Pat. No. 3,96.0,830; U.S. Pat. No. 4,415,665; U.S. Pat. No. 4,412,989; U.S. Pat. No. 4,002,531; U.S. Pat. No. 4,414,147; U.S. Pat. No. 3,788,948; U.S. Pat. No. 4,732,863; U.S. Pat. No. 4,745,180; EP No. 152,847; EP No. 98,110 (published Jan. 11, 1984); JP No. 5,792,435.

Another aspect of the invention is formulations that provide for the sustained release of GH antagonist. Examples of such sustained release formulations include composites of biocompatible polymers, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al., *Polymers for Advanced Technologies* 3:279–292 (1992). Additional guidance in selecting and using polymers in pharmaceutical formulations can be found in the text by M. Chasin and R. Langer (eds.), "Biodegradable Polymers as Drug Delivery Systems, " Vol. 45 of "Drugs and the Pharmaceutical Sciences," M. Dekker, New York, 1990. Liposomes may also be used to provide for the sustained release of GH antagonists. Details concerning how to use and make liposomal formulations of drugs of interest can be found in, among other places, U.S. Pat. No 4,944,948; U.S. Pat. No. 5,008,050; U.S. Pat. No. 4,921,706; U.S. Pat. No. 4,927,637; U.S. Pat. No. 4,452,747; U.S. Pat. No. 4,016,100; U.S. Pat. No. 4,311,712; U.S. Pat; No. 4,370,3.49; U.S. Pat. No. 4,372,949; U.S. Pat. No. 4,529,561; U.S. Pat. No. 5,009,956; U.S. Pat. No. 4,725,442; U.S. Pat. No. 4,737,323; U.S. Pat. No. 4,920,016. Sustained release formulations are of particular interest when it is desirable to provide a high local concentration of GH antagonist, e.g., in an eye chamber for diabetic or proliferative retinopathy, near a tumor, etc.

The present invention is not limited to any particular method of producing the desired GH antagonists. Preferably, these antagonists are produced by first altering a gene encoding a vertebrate GH (e.g., bGH or hGH) having the "native" third alpha helix by site-specific mutagenesis, and then cloning and expressing the altered gene in a suitable host Molecular biology techniques are described in, e.g., Sambrook et al., *Molecular Cloning: A Laboratory Manual* (Cold Spring Harbor Lab Press; 2nd ed., 1989). The gene may be of genomic origin, it may be cDNA prepared from bGH messenger RNA, it may be synthetic, or it may be a combination thereof. For the amino acid sequence of bGH and for the cDNA sequence of the bGH gene, see Miller et al., J. Biol. Chem. 255:7521–24 (1980). For the genomic bGH sequence, see Woychick et al., Nucleic Acids Res. 10:7197–7120 (1982). The cDNA sequence for hGH is given by Chang et al., Gene 55:189 (1987) and DeNoto et al., Nucleic Acid Res. 9:3719 (1981), and the genomic hGH sequence is in Robbins et al., Cell 29:623 (1982).

The host may be any convenient organism, including a bacterial, yeast, insect, or mammalian cell. The gene is operably linked to a promoter functional in the host. A constitutive promoter would activate gene expression in a general manner, i.e., in many tissue and at all times during development. A regulatable promotor may be activated in a tissue or cell specific manner, at a precise time during development, or in response to changes in the environment. A constitutive promoter is usually employed when larger amounts of gene product are required or when the gene product is required in many cells or in many tissues. A regulatable promoter is utilized when one gene product is required in a small number of cells of a particular tissue or at a given time during development.

The expression system may be engineered so that the antagonist is secreted into the culture medium, or the host cells may be grown to a high cell density and then lysed to release the compound.

One method suitable for the purification of bGH (G119R) and the like is described in Leung et al., Endocrinology 119:1489–1496 (1986). Essentially, this procedure involves purification by (a) ammonium sulfate precipitation, (b) fractionation on DEAE-cellulose (or any equivalent ion-exchange column), and (c) gel filtration (e.g., on a Sephadex G-25 and/or Sephacryl S-200 column). Other procedures applicable to purification of GH-related compounds are set forth in Reichert, Jr., "Purification of Anterior Pituitary Hormones: Bovine, Rat and Rabbit," Meth. Enzymol. 37:360 et seq. (Academic Press, N.Y.:1975). Polyclonal or monoclonal antibodies which specifically recognize the protein of interest may also be used in the purification process.

The invention provides for methods for the treatment of; several diseases wherein-the method comprises the step of administering an effective amount of one or more GH antagonists. The diseased tissues or systems which can be treated by the present invention all express GHRs. In humans, since the expression of GHRs is ubiquitous, i.e., found in nearly all human tissues; the range of diseased tissues and organ systems which can be treated by the present invention is very broad. Mercado et al., J. Clin. Endocrinol. and Metabol. 78:731–735 (1993).

The term "treatment" as used herein with reference to a disease is used broadly and is not limited to a method of curing the disease. The term "treatment" includes any method that serves to reduce one or more of the pathological effects or symptoms of a disease or to reduce the rate of progression of one or more of such pathological effects or symptoms. Diseases that may be treated by the methods of the invention are diseases characterized by one or more of the following criteria: elevated levels of GH production, elevated levels of GHR production, and elevated cellular response of GHRs to GH. The term "elevated" as used herein is used with respect to the normal levels of GH production, GHR production, or GH-mediated cellular response in a tissue (or tissues) of a diseased person (or animal) as compared to level in a normal individual. Diseases that may be treated by the methods of the invention include, but are not limited to, acromegaly, gigantism, cancer, diabetes, vascular eye diseases (diabetic retinopathy, retinopathy of prematurity, age-related macular degeneration, retinopathy of sickle-cell anemia, etc.) as well as nephropathy.

Cancers that may be treated by the subject method include, but are not limited to, cancers comprising tumor cells that express GHRs. Cancers that maybe treated by the methods of the invention include, but are not limited to:

Cardiac: sarcoma (angiosarcoma, fibrosarcoma, rhabdomyosarcoma, liposarcoma), myxoma, rhabdomyoma, fibroma, lipoma and teratoma Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinbid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma)

Genitourinary tract: kidney (adenocarcinoma, Wilm's tumor [nephroblastoma], lymphoma, leukemia), bladder and urethra (squamous.cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma)

Liver: hepatoma (hepatocellular carcinoma), cholangiocarcinoma, hepatoblastom, angiosarcoma, hepatocellular adenoma, hemangioma Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochronfroma (osteocartilaginous exostoses), benign chondroma, chondroblastoma, choridromyxofibroma, osteoid osteoma and giant cell tumors Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiforme, oligodendroglioma, schwannoma, retinoblastoma, congenital tumors), spinal cord (neurofibroma, meningioma, glioma, sarcoma)

Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, endometrioid tumors, celioblastoma, clear cell carcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma)

Hematologic: blood (myeloid leukemia [acute and chronic], acute lymphoblastic leukemia, chronic lymphocytic leukemia, myeloproliferative diseases, multiple-myeloma, myelodysplastic syndrome), Hodgkin's disease, non-Hodgkin's lymphoma [malignant lymphoma]

Skin: malignant melanoma, basal cell carcinoma, squamous cell carcinoma, Karposi's sarcoma, moles, dysplastic nevi, lipoma, angioma, dermatofibroma, keloids, psoriasis Adrenal glands: neuroblastoma Another aspect of the subject invention is the discovery that many cancerous cells produce GH. The production of GHs from cancerous cells may have the same adverse effects as excess GH produced by the pituitary gland. Although not wishing to be bound by any particular theory of operation, GH secreted by cancerous cells may manifest pathological effects by means of autocrine stimulation of GHRs on the cancerous cells that secrete GH. GH produced by cancerous cells has a high effective concentration near the site of production. This high effective concentration of GH may serve to stimulate GHRs on cancerous cells at or near the site of GH production. Stimulation of GH receptors on cancerous cells may cause proliferation of the cancer.

The autocrine model of cancer cell GHR stimulation described above suggests that various cancers may be treated by GH antagonists that can interfere with the autocrine stimulation of GHRs on cancer cells. The GH antagonists described herein may be used to treat cancers in which at least some of the tumor cells produce GH. In addition to providing methods for the treatment of cancer with the subject GH antagonists, the invention also contemplates the treatment of various types of cancers by methods comprising the step of administering an effective amount of GH antagonists not specifically described herein.

Furthermore, it is preferable to use GH antagonists derived from a vertebrate species that is the same as the species that is being treated. Alternatively, the methods of treatment may use other compounds that have GH antagonist properties in the treatment methods.

The purified antagonist may be combined with compatible, nontoxic pharmaceutical excipients and administered to an-animal, e.g., to treat a condition characterized, by an excessive.growth rate. (The term "animal" is intended to include humans.) In the case of administration to nonhuman animals, it may be preferable to incorporate the drug into the animal's feed, possibly in a prepared combination of drug and nutritional material ready for use by the farmer. The antagonist may be administered orally, rectally, transdermally, by pulmonary infiltration, insufflation or parenterally (including intravenously, subcutaneously and intramuscularly) to humans, in any suitable pharmaceutical dosage form. In the case of treatment of retinopathy, it may be administered directly onto or into the eye by means of a conventional ocular pharmaceutical form.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Primary among these is the amount of GH secreted by the pituitary, which is on the order of 0.5 mg/day for healthy adult humans. Additional factors include the size of the patient, the age of the patient, the general condition of the patient, the particular disease being treated, the severity of the disease, the presence of other drugs in the patient, the in vivo activity of the antagonist and the like. The trial dosages would be chosen after consideration of the results of animal studies and the clinical literature with respect to administration of GHs, and of somatostatin (a GH release inhibitor). It will be appreciated by the person of ordinary skill in the art that information such as binding constants and Ki derived from in, vitro GH binding competition assays-may also be used in calculating dosages.

A typical human dose of a GH antagonist would be from about 0.1 mg/day to about 10 mg/day, preferably from about 0.5 mg/day to about 2 mg/day, and most preferably about 1 mg/day.

The invention also provides pharmaceutical formulations for use in the subject methods of treating disease. The formulations comprise at least one GH antagonist, preferably a GH antagonist specifically provided for herein, and a pharmaceutically acceptable carrier. A variety of aqueous carriers may be used, e.g., water, buffered water, 0.4% saline, 0.3% glycine, and the like. The pharmaceutical formulations may also comprise additional components that serve to-extend the shelf-life of pharmaceutical formulations, including preservatives, protein stabilizers, and the like. The formulations are preferably sterile and free of particulate matter (for injectable forms). These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate, etc. The formulations of the invention may be adapted for various forms of administration, including intramuscularly, subcutaneously, intravenously, intraocularly, and the like. The subject formulations may also be formulated so as to provide for the sustained release of GH antagonist. Actual methods for preparing parenterally administrable compositions and adjustments necessary for administration to subjects will be known or apparent to those skilled in the art and are described in more detail in, for example, Remington's *Pharmaceutical Science. 17th Ed.*, Mack Publishing Company, Easton Pa. (1985), which is incorporated herein by reference.

In another embodiment the gene is introduced into a host cell which is developed into genetically transformed cells of a transgenic animal. Linearized DNA bearing the GH antagonist gene may be introduced into a gamete, or microinjected into the pronuclei of fertilized eggs, into the cytoplasm, into the nuclei of two-cell embryos, into individual cells of a blastocyst, or into the blastocoel cavity. (Some of these targets may be reached by electroporation instead of microinjection.) Alternatively, a retrovirus bearing the gene may be constructed and used to infect preimplantation embryos or tissue culture cells (e.g., embryonic stem cells) which may be aggregated with such embryos. In either case, the genetically modified zygote, after a brief in vitro cultivation, is implanted into a foster mother and carried to term. For "gene therapy" post partum, see Cline et al., Nature 284:422–425 (1980); Williamson, Nature 298:416–18 (1982). Again the gene is operably linked to a promoter functional in the host, and the promoter may be constitutive or regulatable. Preferably, expression is regulated so abnormal embryonic or fetal development is avoided.

The invention is further illustrated, without limitation, by the following examples.

EXAMPLE 1

Generation of Mutations Conferring the Reduced Growth Phenotype

The plasmid, pBGH-10Δ6, was derived from pBGH-10 and contains the complete coding region of bGH and intron A. bGH introns B, C and D are absent (FIG. 1). This plasmid encodes "wild-type" bGH, and its expression is controlled by a 1700 base pair segment of the mouse metallothionein I transcriptional regulatory sequence.

Plasmids pBGH-10Δ6-G119R and pBGH-10Δ6-E117L, 119R,A122D were derived from pBGH-10Δ6 and were generated by segment-directed mutagenesis using complementary oligonucleotides to replace the DNA between the Tth111I site (found near the 3' end of Exon IV) and the Xma I site (located near the 5' end of Exon V). The other mutations described herein were generated similarly.

The complementary oligonucleotides used for pBGH-10Δ6-G119R were:

(5'GTGTCTATGAGAAGCTGAAGGACCTGGAG
AAAGGATCCTGGCCCTGATGCGG-
GAGCTGGAAGATGGCACCCC 3'; 73-mer) and
(5'CCGGGGGGTGCCATCTTCCAGCTCCCGCA
TCAGGGCCAGGATCCTTTCCTCCAGGTC-
CTTCAGCTTCTCATAGACA 3'; 76-mer).

The complementary oligonucleotides used for pBGH-10Δ6-E117L,G119R,A122D were:

(5' GTGTCTATGAGAAGCTGAAGGACCT-
GCTGGAAAGGATCCTGGACCTGATGCGG-
GAGCTGGAAGATGGCACCCC 3'; 73-mer) and
(5'CCGGGGGGTGCCATCTTCCAGCTCCCGC
ATCAGGTCCAGGATCCTTTCCAGCAG-
GTCCTTCAGCTTCTCATAGACA 3'; 76-mer).

These oligonucleotides hybridize as follows:

```
G119R
 GT GTC TAT GAG AAG CTG AAG GAC CTG GAG GAA AGG ATC CTG GCC

ACA CAG ATA CTC TTC GAC TTC CTG GAC CTC CTT TCC TAG GAC CGG

Arg Val Tyr Glu Lys Leu Lys Asp Leu Glu Glu Arg Ile Leu Ala

CTG ATG CGG GAG CTG GAA GAT GGC ACC CC

GAC TAC GCC CTC GAC CTT CTA CCG TGG GGG GCC

Leu Met Arg Glu Leu

E117L, G119R, A122D
 GT GTC TAT GAG AAG CTG AAG GAC CTG CTG GAA AGG ATC CTG GAC

ACA CAG ATA CTC TTC GAC TTC CTG GAC GAC CTT TCC TAG GAC CTG

Arg Val Tyr Glu Lys Leu Lys Asp Leu Leu Glu Arg Ile Leu Asp

CTG ATG CGG GAG CTG GAA GAT GGC ACC CC

GAC TAC GCC CTC GAC CTT CTA CCG TGG GGG GCC

Leu Met Arg Glu Leu
```

These oligonucleotides encode DNA changes which result in the substitutions of Arg for Gly at position 119 in pBGH-10Δ6-G119R; and Leu for Glu at position 117, Arg for Gly at position 119 and Asp for Ala at position 122 in pBGH-10Δ6-E117L,G119R,A122D. These amino acids were chosen because they have hydrophilic (Arg and Asp) of hydrophobic (Leu) character [see Hopp and Woods, Proc. Natl. Acad. Sci. USA 78:3924–28 (1981)], positively (Arg) or negatively (Asp) charged side chains [see Kaiser and Kezdy, Science 223:249–55 (1984)], and high alpha helix-forming potential [see Chou and Fasman, Ann. Rev. Biochem. 47:251–76 (1978)] furthering generation of an idealized amphiphilic alpha helix [see Margalit et al., J. Immunol. 138:2213–29 (1987); Brems et al., Biochemistry 26:7774–78 (1987); Kaiser and Kezdy, supra; Chen et al., Proc. Natl. Acad. Sci. USA 87:5061–65 (1990)]. In addition, these oligonucleotide duplexes encode a silent base-pair change designed to create a unique BamH1 restriction site which simplified screening procedures. The oligonucleotides were annealed and subcloned between the Tth111I and XmaI sites using standard procedures. Maniatis et al., Molecular Cloning (Cold Spring Harbor) (1982). Mutant plasmid DNAs were identified by digestion with BamH1.

The nucleotide sequence of the mutated bGH target regions were determined by using the dideoxy chain-termination method with modified T7 DNA polymerase (Sequenase, United States Biochemical; Sanger et al., Proc. Natl. Acad. Sci. USA 74:5463–67 (1977)). Oligonucleotide primers for manual DNA sequencing were synthesized using the DuPont Coder #300 DNA synthesizer and purified by denaturing polyacrylamide gel electrophoresis, passive elution and concentration by ethanol precipitation. The oligonucleotide primers used for the direct sequencing analysis of the two mutants was the following: 18-mer (5'AAATTTGTCATAGGTCTG 3'). Briefly, 1–3µg of double-stranded plasmid DNA was denatured in the presence of 0.2N NaOH, and 10–20 pmoles of oligonucleotide primer was allowed to anneal (65° C., 2 min. followed by 30 min. slow cool) to the denatured template. A two-step polymerization was performed by using the modified T7 DNA polymerase which extends the oligonudleotide-primed chain in the presence of dNTP's and deoxyadenosine triotriphosphate (>1000 Ci/mmole, Amersham) followed by transfer of equal aliquots into each of four specific dideoxynucleotide mixes which randomly terminate chain elongation. Following addition of a formamide termination buffer to each reaction, the samples were incubated at 80° C. for 2 min. and the DNA sequence was determined after size fractionation of the four sets of fragments by 10% polyacrylamide/8M urea electrophoresis and autoradiography.

EXAMPLE 2

Expression in Mammalian Cells in Culture

Using the in vitro mutagenesis protocols described above, two mutant bGH genes were generated initially: one converts Gly-119 to Arg (G119R) and the second converts Glu-117 to Leu, Gly-119 to Arg, and Ala-122 to Asp (E117L,G119R;A122D).

The plasmids encoding these mutations as well as wild-type bGH DNA (pBGH-10Δ) were transiently introduced into cultured mouse L cells, which were subsequently analyzed for bGH expression. Following "western analysis", protein bands of approximately 22,000 daltons were observed for wild-type bGH and bGH derived from the two mutant genes.

Mouse L cells were maintained in DMEM (Gibco) plus 10% calf serum.and 25 µg/ml gentamicin (Gibco). In this study, a modification of a previously described transfection procedure was employed. Lopaca et al., Nucleic Acids Res., 12:5707–5717 (1984). Briefly, 2 µg of plasmid DNA was added to 1.0 ml of DMEM containing 0.2 mg DEAE-dextran. This solution was added to approximately 106 cells in a 35-mm tissue culture plate which had been washed previously with 2.0ml of DMEM. Following incubation of the cells for 1 hour at 370° C., the DNA-DEAE-dextran solution was removed and the cells "shocked" for 90 seconds with 2.0 ml of 10 DMSO in Hepes buffered saline, at room temperature. Subsequently, the "shock" solution was removed and cells washed with 2.0 ml DMEM. Media containing 10% Nu-Serum (Collaborative Research) plus 50 µ/ml gentamicin were changed daily. Culture fluids were stored at −20° C. For bGH binding assays, transfected cells were incubated in DMEM minus serum for 16 hours, after which the culture fluids were removed and frozen at −20° C.

Sodium dodecyl sulfate (SDS) PAGE analyses of secreted bGH have been described. Kopchick et al., DNA 4:23–31 (1985); Kelder et al., Gene 76:75–80 (1989). In this study, we used a polyclonal anti-bGH serum for "western" analysis.

EXAMPLE 3

GH Receptor Binding Studies

Culture fluids lacking serum were collected from cells transfected by pBGH10Δ6 (wild-type bGH) and the mutant bGH genes. Following lyophilization of the culture media and bGH concentration determinations, competitive membrane binding studies were carried out as previously described. Smith and Talamants, J. Biol. Chem. 262:2213–19 (1987). Liver membrane preparations from C57BL/6JxSJL hybrid mice of either sex (60–120 days old) were homogenized with a Brinkman Polytron in 4 volumes (w/v) of 0.3 M sucrose, 10 mM EDTA,. 50 mM Hepes, 0.1 mM TPCK and lmM PMSF at pH 8.0; The above step and all the following protocols were carried out at 4° C. The homogenate was centrifuged at 20,000×g for 30 min. and the supernatant was centrifuged at 100,000×g for 1 hour. The pellets were washed once with 10 mM Hepes, pH 8.0 and recentrifuged. These pellets were resuspended in 10 mM Hepes, pH 8.0, to a protein concentration of approximately 50 mg/ml. These membranes were aliquoted, frozen on dry ice, and stored at −20° C. Membrane protein concentrations were determined by the Lowry protein assay. Lowry et al., J. Biol. Chem. 193:265–275 (1951).

Competitive binding assays were performed using the following protocol. Microsomal membranes corresponding to three mgs. protein were incubated with 30,000 cpm/tube $^{125}$I-bGH (Cambridge Medical Diagnostics) and unlabeled bGH ranging from 0.3 ml assay buffer (20 mM Hepes, 10 mM $CaCl_2$ 0.1% BSA, and 0.05% $NaN_3$ pH 8.0). All assays were performed in triplicate. After overnight incubation at room temperature, membrane bound hormone was separated from free hormone by the addition of 1 ml of ice cold assay buffer followed by centrifugation at 10,000×g for 20 min. Membrane pellets were then assayed for radioactivity. Specifically bound radioactivity was determined by subtraction from the value produced by incubation of membranes with 5 µg unlabeled bGH. Smith and Talamants (1987).

Effective doses which resulted in 50% displacement (ED50) of $^{125}$I-bGH from the membrane preparations were determined. Mutant bGH encoded by pBGH-10Δ6-G119R and PBGH-10Δ6-E117L,G119R,A122D revealed an ED50 value similar to wild-type bGH.

EXAMPLE 4

Transgenic Mouse Production Pilot Study

A series of transgenic mouse lines which contain wild-type and mutant bGH genes were produced by standard microinjection techniques. McGrane et al. (1988). DNA extraction from mouse tails, dot blots, and serum determinations was as described. McGrane et al. (1988).

The genes contain the transcriptional regulatory sequence of the mouse metallothionein I promoter which has been shown to be active in liver tissue as well as other tissues of the transgenic mouse. Palmiter et al., Nature 300:611–615 (1982). Offspring generated by the microinjection procedure were assayed for bGH DNA by slot blot hybridization analysis. Mouse lines were generated which contain-approximately one copy of the recombinant bGH DNA sequences derived from pBGH-10Δ6 (wild-type), pBGH-10Δ6-G119R, and pBGH-10Δ6-E117L,G119R,A122D. Serum from transgenic animals were assayed for bGH levels by the Western technique. All mice which expressed the wild-type bGH transgene in serum also possessed a corresponding enhanced growth rate. Mice which expressed mutant bGH (G119R or E117L,G119R,A122D) in serum were dramatically and significantly smaller. After eight weeks' growth, the growth ratio for wild-type bGH transgenic mice relative to control littermates was mice relative to control littermates was 1.5 while the ratio for the two bGH mutant mice to control littermates was -0.6. In the case of the triple mutant, we generated 10 founder mice that express the mutated bGH gene. The growth between the transgenic and nontransgenic littermates ranged from 0.58 to 1.00. The degree of suppression of growth was directly related to the serum levels of the mutated bGH. Three founders have been bred that pass the trait to offspring; about 50% of these offspring are positive for the gene and possess the corresponding small phenotype.

It has been demonstrated that many activities of GH are mediated through family of peptides known as insulin-like growth factors ("IGFs"), in particular IGF-1, which is believed to be produced primarily in the liver following GH binding to its receptor(s). Truesch et al., Ann Rev. Physiol. 47:44367 (1985); Zapt et al., Harm Res. 24:121–130 (1986). IGF-1 has been shown to decrease GH production in the pituitary by a,classical negative feedback mechanism. Leung et al., Endocrinology 119:1489–96 (1986). One hypothesis to explain the growth suppression in pBGH-10Δ6-M8 transgenic mice is that bGH-M8 is active as an in vivo antagonist to mouse GH (mGH), thereby suppressing mouse IGF-1 production. If this is true, then one would expect not only a reduction in serum mouse IGF-1 levels in bGH-M8 transgenic mice but also an increases in mGH production in the pituitary. We have found that the IGF-1 levels in the serum of the "small" transgenic mice are about 50% those of normal nontransgenic mice while mice containing wild-type bGH (large mice) have approximately 2× the IGF-1 levels of nontransgenic mice. Results from immunoblot analysis of whole pituitary glands taken from bGH-M8 transgenic mice, bGH transgenic mice, and their nontransgenic littermates suggest that the pituitary glands in those growth-suppressed mice contain higher levels of mGH relative to their nontransgenic littermates. In contrast, mGH levels in bGH transgenic mice were largely depressed because mouse serum IGF-1 levels were increased up to twice as much as levels in serum of their nontransgenic littermates. Palmiter et al. Science 222:809–14 (1983). Together, these results indicate that the altered bGH molecules are acting as an antagonist to endogenous mouse GH. Thus, it is the first example to our knowledge of an in vivo GH antagonist and the first example of uncoupling of growth-promoting and receptor-binding activities of GHs.

EXAMPLE 5

Screening of Other Muteins of bGH and hGH

By similar procedures, muteins, of bGH and hGH with alterations in the third alpha helix have been prepared and tested for secretion in L cells, and, in selected cases, their effect on the growth of transgenic mice, with the following results.

The mutants are described by giving the original amino acid, its position in the amino acid sequence of bGH, and the replacement amino acid, with the amino acids set forth according to the internationally accepted single letter code. George et al., Protein Seq. Data Anal. 1:27–39 (1987).

A first set of mutated bGH genes, when expressed in transgenic mice, resulted in animals with a growth ratio similar to that of mice which express wild-type bGH (i.e., 1.59–1.72). We have referred-to these analogs as "full functional agonists" (Table I).

A second set of mutated bGH genes, when expressed in transgenic mice, resulted in mice with a growth ratio smaller than those animals which express wild-type bGH (i.e., 1.29–1.35). We refer to these bGH analogs as "partial functional agonists" and have listed them Table II.

A third set of mutated bGH genes, when expressed in transgenic mice, resulted in animals with a growth ratio similar to nontransgenic mice (i.e., 1.0). We refer to these analogs as "non-functional agonists" (Table III).

A fourth set of mutated bGH genes, when expressed in transgenic mice, resulted in mice a growth ratio of between 0.57 and 1.0 (Table IV). The growth ratio of the mice was negatively correlated with the serum level of the bGH analog, i.e., as the serum level of the bGH analogue increased, the growth ratio of the animals decreased. This correlation is shown graphically in FIG. 13.

Also, these analogs, when expressed to NIH-3T3-preadipocytes, did not result in stimulation of preadipocytes differentiation; however, native GH will promote this differentiation (FIG. 12). In fact, these analogs will antagonize the ability of wild-type GH to promote preadipocyte differentiation (FIG. 11). We have referred to these analogs as "functional antagonists" (Table IV).

We have also generated transgenic mice which express either wild-type hGH, hGH G120A, hGH G120R and hGH G120W (Table V). Mice which express hGH G120A show a growth-enhanced phenotype similar to mice which express wild-type hGH (Table V). We call this hGH analogue a "functional agonist." In contrast, substitution of R or W for G at position 120 in hGH, and subsequent expression in transgenic mice, results in animals with a growth ratio between 073 and 0.96 (Table V), and whose level of serum hGH analogs is negatively correlated with the growth phenotype, i.e., as the serum levels of these hGH 120 analogs increase, the growth ratios decrease. This correlation is shown in FIG. 14. Therefore, like the bGH analogs which act as "functional antagonist," we termed these hGH120 analogs as "functional antagonist." It is important to note that the Gly residue in bGH at position 119 is the homologue of the Gly residue in hGH at position 120. They are both located in the central portion of the third alpha helix.

A subset bGH analogs is presented in Table VI in which we have evaluated their ability to be secreted following transfection of the mutated DNA into mouse L cells. Transgenic animals have not been generated which contain these mutated DNAs.

The mutant K112L,K114W shows the effect of expanding the hydrophobic face of the helix. This mutant affects animal growth much as does wild-type GH.

The mutations K114P, E118P and L121P (and various combinations thereof) apparently destroy the alpha helix. (Pro is a strong alpha helix breaker.) The growth-related biological activity is abolished. The mutation E126G is a special case; Gly is a helix breaker, but position 126 is at the end of the helix so the normal biological activity is retained. With G119P, however, one strong helix breaker was substituted for an even stronger one; the alpha helix was apparently preserved.

The third alpha helix of wild-type GH diverges from a perfect amphiphilic alpha helix at three positions. First, at bGH position 117, Glu is a hydrophilic amino acid in the hydrophobic face, Second, at bGH position 119, Gly is a neutral amino acid in the hydrophilic face. Finally, at bGH position 122, Ala is a hydrophobic amino acid in the hydrophilic face. The mutations E117L, ,G119R and A122D, separately or in combination, increase the amphiphilic character of the helix. G119R additionally increases the alpha-helical tendencies of the sequence. Our initial hypothesis was that the growth-inhibitory activity of the mutants G119R and E117L,G119R,A122D was associated with the increased amphipathicity of the third alpha helix. We have since developed evidence that the amphipathicity of the third alpha helix is largely irrelevant to that activity.

(1) The single E117L mutation, like wild-type bGH, produced large animals.
(2) Mutant G119P-produced the small animal phenotype even though Pro is as hydrophilic as Gly.
(3) Mutant G119L produced the small animal phenotype, even though Leu is hydrophobic and therefore disrupts the hydrophilic face of the helix.
(4) Mutant E111L,G119W,R125L produced the small animal phenotype even though all three mutations disrupt the hydrophilic face of the helix.
(5) The single A122D mutation produces a mutein which has no effect on growth.

Thus, in one embodiment, the present invent-ion relates to mutations of the third alpha helix which result in growth-inhibitory activity yet reduce or leave unchanged the amphiphilic character of the helix.

Additional GH antagonists may be identified by systematically varying the codon corresponding to G119 in bGH, so as to express the 18 other mutants having a single amino acid change at.this position. This is readily accomplished by synthesizing oligonucleotides differing from those set forth in Example 1 at codon 119 so as to encode the desired alternative amino acid. Similarly, one may alter the homologous Glyc residue in the third alpha helix of other GHs, e.g., the G120 of hGH. By similar means, variations of the codons corresponding to other amino acids of the third alpha helix of a GH are investigated.

EXAMPLE 6

Anticholesterolemic Activity of GH Antagonists
Procedures for Clinical Chemistry Tests:

Blood samples were obtained from mouse tails. The samples were allowed to clot at room temperature for 5 minutes and were then centrifuged and the serum was collected and frozen at $-20°$ C. until analysis. Total Cholesterol (TC), Triglyceride (TR), Glucose (GL), and Blood Urea Nitrogen (BUN) were analyzed on a Kodak Ektachem DT 60 Analyzer using dry, multilayered, self-contained elements specific for each test. 10 $\mu l$ of serum was pipetted on individual slides specific for each test and were analyzed using calorimetric measurement by reflectance spectrophotometry methods and compared to daily quality control reference samples. Results:

There is no significant difference in blood glucose, serum urea/nitrogen and serum triglyceride levels between bGH-M8 transgenic mice and their nontransgenic littermates. However, total serum cholesterol levels in bGH-M8 transgenic mice are significantly decreased ($p<0.05$) as compared to their nontransgenic littermates and bGH transgenic mice.

EXAMPLE 7

In Vitro Bioassay for GH Antagonist Activity

Studies of GH have shown that it promotes the formation of adipose from preadipose 3T3 cells. Nurikawa et al., Cell 29:789 (1982). Glycerophosphate dehydrogenase (GPDH) has been used as a differentiation marker for this GH-induced adipose conversion. Wise and Green, J. Biol. Chem. 254:273–75 (1979); Nixon and Green, Endocrinology 114:527 (1984); Pairault and Green, Proc. Natl. Acad. Sci. USA 76:5138 (1979).

We have adapted this assay to determine whether a bGH mutant acts as a GH antagonist. Both bGH and bGH-M8 bind to receptors on these preadipocytes with a Kd value of 10 mM. When exposed to native sequence bGH (30 pM) and cultured for seven days, the preadipocytes differentiate and GPDH activity is stimulated. If the bGH mutant is added to culture medium containing wild-type bGH, there is a dose dependent reduction in GDPH activity and therefore, presumably, in adipose conversion (FIG. 11).

This assay is a convenient screening tool for identifying potential GH antagonists.

EXAMPLE 8

Mice transgenic for the wild-type bGH gene are known to develop progressive severe glomerulosclerosis and increased glomerular size. Doi et al., Am. J. Path. 137:541–52 (1990); Resce et al., Lab. Invest. 65:601–5 (1991); Doi et al., Am. J. Path. 131:398–403 (1988); see also Stewart et al., Endocrinology 130:405–414 (1992). This is not merely a function of-body size, as bGH-M11 mice (i.e., L121P, E126G mutants), whose mutant bGH does not enhance growth, also exhibit glomerulosclerosis. In bGH-M8 (G119R) mice, however, which had reduced serum IGF-1, body size and glomerular size relative to nontransgenic mice, glomerulosclerosis was absent.

The following summarizes growth ratio comparisons between transgenic mice expressing bGH analogs and their nontransgenic littermates at 6 to 8 weeks of age.

TABLE I

Transgenic mice which express the following bGH analogs exhibited phenotypes similar to transgenic mice which express wild-type bGH (we have termed these analogs "full functional agonists").*

| bGH Analogs | n | Mean Growth Ratio | SD |
| --- | --- | --- | --- |
| wild-type bGH | 7 | 1.61 | 0.14 |
| bGH-E111A | 2 | 1.72 | — |
| bGH-K112L | 12 | 1 70 | 0.19 |
| bGH-K114W | 12 | 1.70 | 0.19 |
| bGH-L116A | 6 | 1.71 | 0.16 |
| bGH-E117L | 13 | 1.68 | 0.18 |
| bGH-A122T | 10 | 1.67 | 0.16 |
| bGH-R125L | 3 | 1.61 | 0.18 |
| bGH-E126G | 4 | 1.59 | 0.14 |

*There is no correlation between serum levels of these bGH analogs and the growth phenotypes. These mutated bGH genes are expressed in mouse L cells and the secretion pattern is similar to the wild-type bGH.

TABLE II

Transgenic mice which express the following bGH analogs exhibited phenotypes smaller than transgenic mice which express wild-type bGH, however, they are larger than nontransgenic mice (we have termed these analogs "partial functional agonists")*

| bGH | n | Mean Growth Ratio | SD |
| --- | --- | --- | --- |
| wild-type bGH | 7 | 1.61 | 0.14 |

TABLE II-continued

Transgenic mice which express the following bGH analogs exhibited phenotypes smaller than transgenic mice which express wild-type bGH, however, they are larger than nontransgenic mice (we have termed these analogs "partial functional agonists")*

| bGH | n | Mean Growth Ratio | SD |
|---|---|---|---|
| D115A | 3 | 1.35 | 0.15 |
| L123I | 3 | 1.29 | 0.13 |

*There is no correlation between serum levels of these bGH analogs and the growth phenotypes. These mutated bGH genes are expressed in and secreted by mouse L cells with the pattern similar to wild-type bGH. Note that for the purposes of Tables I-VI, the characterization of a mutein as "functional" or "non-functional" is in the context of its effect on growth.

TABLE III

Transgenic mice which express the following bGH analogs exhibited phenotypes similar to their nontransgenic littermates (we have termed these analogs as "non-functional agonists")*

| bGH Analogs | n | Mean Growth Ratio | SD |
|---|---|---|---|
| K114P,E118P | 9 | 1.01 | 0.09 |
| L121P,E126G | 11 | 0.94 | 0.06 |
| A122D | 9 | 0.90 | 0.11 |

*There is no correlation between levels of bGH analogs in serum and the growth phenotypes. These mutated bGH genes are expressed in and secreted by mouse L cells with the exceptions of bGH-K114P,E118P and bGH-L121P,E126G which are not secreted by mouse L cells.

TABLE IV

Transgenic mice which express the following bGH analogs exhibited phenotypes smaller than nontransgenic littermates (we have termed these analogs as "functional antagonists")*

| bGH Analogs | Animal # | Sex | Serum bGH (µg/ml) | Growth Ratio (Two Month) |
|---|---|---|---|---|
| E117L,G119R, A122D | 6 | F | 3.4 | 0.58 |
| | 15 | M | 3.3 | 0.69 |
| | 32 | F | 3.7 | 0.57 |
| | 51 | F | 5.1 | 0.63 |
| | 55 | M | 2.1 | 0.85 |
| | 65 | F | 0.6 | 1.0 |
| | 67 | F | 0.6 | 0.87 |
| | 70 | F | 3.3 | 0.70 |
| | 71 | F | 2.6 | 0.70 |
| | 89 | F | 1.8 | 0.85 |
| G119R | 25 | M | 0.5 | 0.93 |
| | 28* | M | 0.9 | 0.88 |
| | 49* | M | 6.0 | 0.60 |
| | 53 | M | 1.5 | 0.85 |
| | 94 | F | 0.2 | 0.98 |
| | 138 | F | 3.0 | 0.74 |
| G119P | 9 | F | 2.0 | 0.81 |
| G119K | 10 | M | 0.5 | 0.84 |
| | 12 | M | 0.4 | 0.95 |
| | 18 | F | 4.0 | 0.78 |
| | 26 | F | 5.0 | 0.59 |
| G119L | 23 | F | 6.5 | 0.81 |
| | 27 | M | 0.5 | 1.0 |
| G119W | 16 | M | 8.0 | 0.64 |
| G119Δ | 14 | M | 0.5 | 0.96 |
| | 15 | M | 0.5 | 0.90 |

TABLE IV-continued

Transgenic mice which express the following bGH analogs exhibited phenotypes smaller than nontransgenic littermates (we have termed these analogs as "functional antagonists")*

| bGH Analogs | Animal # | Sex | Serum bGH (µg/ml) | Growth Ratio (Two Month) |
|---|---|---|---|---|
| | 22 | M | 8.0 | 0.75 |
| | 23 | M | 0.5 | 0.90 |

*The level of mouse growth suppression is correlated with serum levels of analogs (see FIG. 13). These mutated bGH genes are expressed in and secreted mouse L cells. The secretion pattern is similar to wild-type bGH.

TABLE V

Summary of transgenic mice which express hGH genes encoding single amino acid substitutions at position 120* (hGH-G120A is a "full-functional agonist". (hGH-G120R and hGH-G120W serve as "functional antagonists").

| hGH Analogs | Animal # | Sex | Serum hGH (µg/ml) | Growth Ratio (Two Month) |
|---|---|---|---|---|
| wild-type hGH | 7 | | | 1.62 ± 0.15 |
| G120A | 95 | M | 3.9 | 1.48 |
| | 6 | F | 21.5 | 1.76 |
| G120R** | 20 | F | 78.5 | 0.79 |
| | 48 | F | 1.5 | 0.96 |
| | 68 | M | 3.4 | 0.73 |
| | 73 | F | 0.8 | 0.93 |
| | 92 | F | 1.1 | 0.93 |
| G120W | 18 | M | 5.5 | 0.82 |
| | 39 | M | 2.7 | 0.77 |
| | 56 | F | 2.0 | 0.83 |

*bGH Gly-119 is in a position equivalent to hGH Gly-120. Therefore, we refer to hGH Gly-120 consistently with the literature.
**The level of growth suppression is correlated with serum levels of hGH analogs (see FIG. 14)

TABLE VI

Summary of mutated bGH genes expressed in mouse L cell without transgenic mice data.

| bGH Analogs | L-Cell Secretion |
|---|---|
| wild-type bGH | + |
| K114P | − |
| E118P | − |
| E117,G119R | + |
| E117,A122D | + |
| V109D,Y110D,L116R | + |
| E111L,G119W | + |
| L121R,M124K | + |
| E111L,G119W,L121R,M124K | + |
| D115V | + |
| D115G | + |
| V109D,Y111D,L116R,L121R,M124K | − |
| E111L,G119W,R125L* | + |
| E111L,G119W,L121R,M124K | + |
| V109D,Y110D,L116K,R125L | + |

*This bGH analogue resulted in a mean animal transgenic/nontransgenic growth ratio of 0.7.

TABLE VII

"M" mice mutants

| M1 | (K112L,K114W) |
|---|---|
| M10 | (K114P,E118P) |

TABLE VII-continued

"M" mice mutants

| | |
|---|---|
| M11 | (L121P,E126G) |
| M4 | (E117L) |
| M6 | (G119R) |
| M2 | (A122D) |
| M7 | (E117L,G119R) |
| M3 | (E117L,A122D) |
| M8 | (E117L,G119R,A122D) |

EXAMPLE 9

GH Production in Cancerous Cells

The availability of GH antagonists prompted an inquiry as to whether some or all of the abnormal growth properties of malignant cells result from abnormal sensitivity to GH and/or an abnormal "autocrine" stimulation of GHR by self-produced GH.

To test this hypothesis, malignant cells were examined by reverse transcriptase-polymerase chain reaction (RT-PCR) amplification using GH specific primers. RNA samples of the following tumor types were analyzed: Burkitt's lymphoma, colorectal carcinoma, lung carcinoma, lymphoblastic leukemia, and melanoma. Samples from normal placenta, which produces an hGH variant, and normal mammary gland were used as positive and negative controls, respectively.

The RNAs were purchased from Clontec Laboratories, Inc. (Palo Alto, Calif.) (1995): bone marrow (Cat# 6573–1), brain (Cat# 6516–1), lymph node (Cat# 6594–1), placenta (Cat# 6518–1), prostate (Cat# 6546–1), retina (Cat# 6540–1), salivary gland (Cat# 6534–1), skeletal muscle (Cat# 6541–1), spinal cord (Cat# 6593–1), thymus (Cat# 6536–1), trachea (Cat# 6549–1), colorectal adenocarcinoma (Cat# 6586–1), leukemia lymphoblastic (Cat# 6587–1), lung carcinoma (Cat# 6592–1), lymphoma Burkitt's (Cat# 6531–1) and melanoma (Cat# 25 6591–1). The amplification primers used were 5'-GGGATGCCACCCGGGCAGCTAG-3' (for RT and subsequent PCR) and 5'-CTCAAGGATCCCAAGGCCCAAC-3' (for PCR). The RT reaction was run for 12 min. at 70° C. PCR reactions were run as follows: 1 cycle at 94° C. for 2 min.; 35 cycles at 94° C. for 1 min., at 56° C. for 1min., at 72° C. for 1 min.; 1 cycle at 72° C. for 6 min.

Electrophoresis after the amplification reactions revealed two primer-specific products, one having estimated size, 680 bp, which corresponds to GH mRNA. Subsequent experiments investigated the hybridization of the PvuII fragment of the hGH gene (see Goeddel et al., Nature 281:544–548 (1979)) to the amplification reaction products. The hybridization experiments confirmed that there is a high level of GH expression in lymphoblastic leukemia tissue and placental tissue and also demonstrated more modest levels of expression in melanoma, colorectal carcinoma, Burkitt's lymphoma and lung carcinoma tissues.

To further test the relationship between abnormal autocrine GH activity and malignancy, RT-PCR experiments were conducted to determine whether mRNA encoding a GHR is present in the same malignant cell lines. The primers in the RT-PCR reaction were selected to amplify the intracellular portion of the GHR. Analysis of the reaction products revealed a product in the melanoma and, possibly, the other malignant cell lines which is smaller than the expected product from the full length GHR transcript. Truncated products were also found from several of the normal tissues. The homology of the product to GHR was confirmed by hybridization.

These studies indicate that stimulation of GHR by self-produced GH, which would be susceptible to inhibition by a GH antagonist, could play a role in the abnormal growth characteristics of some malignant cells.

INCORPORATION BY REFERENCE

All patents, patents applications, and publications cited are incorporated herein by reference.

EQUIVALENTS

The foregoing written specification is sufficient to enable one skilled in the art to practice the invention. Indeed, various modifications of the above-described means for carrying out the invention which are obvious to those skilled in the field of molecular biology, medicine or related fields are intended to be within the scope of the following claims.

We claim:

1. A non-naturally occurring vertebrate growth hormone variant having an amino acid sequence comprising an amino acid substitution of any amino acid, other glycine or alanine, for the glycine at the position corresponding to position Gly119 of bovine growth hormone, wherein the growth hormone variant has vertebrate growth hormone inhibitory activity, with the proviso that said variant does not correspond to human growth hormone with all of the following substitutions and no others: Y111V, L113I, K115E, D116Q, E118K, E119R, G120L, Q122E, T123G, G126L, R127I and E129S.

2. A vertebrate growth hormone variant of claim 1 where said variant differs from the vertebrate growth hormone solely at said position corresponding to Gly119 of bovine growth hormone.

3. The vertebrate growth hormone variant of claim 1 having an amino acid sequence comprising lysine at the position corresponding to Gly119 of bovine growth hormone.

4. The vertebrate growth hormone variant of claim 1 having an amino acid sequence comprising arginine at the position corresponding to Gly119 of bovine growth hormone.

5. The vertebrate growth hormone variant of claim 1 having an amino acid sequence comprising proline at the position corresponding to Gly119 of bovine growth hormone.

6. The vertebrate growth hormone variant of claim 1 having an amino acid sequence comprising tryptophan at the position corresponding to Gly119 of bovine growth hormone.

7. The vertebrate growth hormone variant of claim 1 having an amino acid sequence comprising leucine at the position corresponding to Gly119 of bovine growth hormone.

8. A method of inhibiting the development of, ameliorating, or otherwise treating a condition, or ameliorating a growth hormone-mediated symptom of a condition, of a mammal caused, hastened, or exacerbated by a mammalian growth hormone activity, said condition or symptom being responsive to a vertebrate growth hormone variant having growth hormone receptor antagonist activity, which comprises administering to a mammal a growth hormone activity-antagonizing and pharmaceutically acceptable amount of a vertebrate growth hormone variant according to any one of claims 1–7.

9. A method of reducing the activity of growth hormone in a mammal, which comprises administering to a mammal a growth hormone activity-antagonizing and pharmaceutically acceptable amount of a vertebrate growth hormone variant according to any one of claims 1–7.

* * * * *